(12) United States Patent
Cross et al.

(10) Patent No.: US 12,190,707 B2
(45) Date of Patent: Jan. 7, 2025

(54) METHODS AND SYSTEMS FOR IMPROVED ACCURACY IN HAND-HYGIENE COMPLIANCE

(71) Applicant: GOJO Industries, Inc., Akron, OH (US)

(72) Inventors: Tamara M. Cross, Uniontown, OH (US); John Harry Lerner, Hudson, OH (US); Timothy M. Cambier, Uniontown, OH (US)

(73) Assignee: GOJO Industries, Inc., Akron, OH (US)

( * ) Notice: Subject to any disclaimer, the term of this patent is extended or adjusted under 35 U.S.C. 154(b) by 35 days.

(21) Appl. No.: 18/329,006

(22) Filed: Jun. 5, 2023

(65) Prior Publication Data

US 2023/0316893 A1 Oct. 5, 2023

Related U.S. Application Data

(63) Continuation of application No. 17/732,599, filed on Apr. 29, 2022, now Pat. No. 11,704,993, which is a continuation of application No. 17/078,436, filed on Oct. 23, 2020, now Pat. No. 11,348,443.

(60) Provisional application No. 62/924,770, filed on Oct. 23, 2019.

(51) Int. Cl.
  *G08B 21/24* (2006.01)
(52) U.S. Cl.
  CPC ................. *G08B 21/245* (2013.01)
(58) Field of Classification Search
  CPC ...... G08B 21/245; G06Q 50/20; G06Q 50/22; G16H 15/00; G16H 40/20; G16H 40/67
  See application file for complete search history.

(56) References Cited

U.S. PATENT DOCUMENTS

| | | |
|---|---|---|
| 6,344,794 B1 | 2/2002 | Ulrich et al. |
| 6,462,656 B2 | 10/2002 | Ulrich et al. |
| 6,727,818 B1 | 4/2004 | Wildman et al. |
| 6,825,763 B2 | 11/2004 | Ulrich et al. |
| 6,876,303 B2 | 4/2005 | Reeder et al. |
| 7,015,816 B2 | 3/2006 | Wildman et al. |
| 7,034,690 B2 | 4/2006 | Chaco |
| 7,042,337 B2 | 5/2006 | Borders et al. |
| 7,242,306 B2 | 7/2007 | Wildman et al. |
| 7,242,308 B2 | 7/2007 | Ulrich et al. |
| 7,248,933 B2 | 7/2007 | Wildman |
| 7,319,386 B2 | 1/2008 | Collins, Jr. et al. |

(Continued)

FOREIGN PATENT DOCUMENTS

WO 2005045461 A1 5/2005

OTHER PUBLICATIONS

US 8,773,268 B2, 07/2014, Wildman et al. (withdrawn)

*Primary Examiner* — An T Nguyen
(74) *Attorney, Agent, or Firm* — Calfee, Halter & Griswold LLP

(57) ABSTRACT

Exemplary embodiments of methods and devices for obtaining more accurate hand hygiene compliance metrics are disclosed herein. An exemplary device or badge for a hygiene compliance system includes a housing; a processor located in the housing; memory in circuit communication with the processor; wireless communication circuitry in circuit communication with the processor; and an additional time input in circuit communication with the processor.

20 Claims, 9 Drawing Sheets

(56) References Cited

U.S. PATENT DOCUMENTS

| | | |
|---|---|---|
| 7,408,470 B2 | 8/2008 | Wildman et al. |
| 7,443,302 B2 | 10/2008 | Reeder et al. |
| 7,450,024 B2 | 11/2008 | Wildman et al. |
| 7,679,520 B2 | 3/2010 | Zerhusen et al. |
| 7,734,476 B2 | 6/2010 | Wildman et al. |
| 7,812,730 B2 | 10/2010 | Wildman et al. |
| 7,907,053 B2 | 3/2011 | Wildman et al. |
| 8,334,777 B2 | 12/2012 | Wilson et al. |
| 8,368,544 B2 | 2/2013 | Wildman et al. |
| 8,598,996 B2 | 12/2013 | Wildman et al. |
| 8,779,924 B2 | 7/2014 | Pesot et al. |
| 8,803,669 B2 | 8/2014 | Schuman, Sr. et al. |
| 9,213,956 B2 | 12/2015 | Huster et al. |
| 9,240,120 B2 | 1/2016 | Girardeau et al. |
| 9,349,267 B2 | 5/2016 | Wildman et al. |
| 9,396,638 B2 | 7/2016 | Wildman et al. |
| 9,418,536 B1 | 8/2016 | Felch et al. |
| 9,659,148 B2 | 5/2017 | Girardeau et al. |
| 9,715,817 B2 | 7/2017 | Wildman et al. |
| 9,721,452 B2 | 8/2017 | Felch et al. |
| 9,773,403 B2 | 9/2017 | Morgan et al. |
| 9,830,764 B1 | 11/2017 | Murphy |
| 9,836,942 B2 | 12/2017 | Wiggermann et al. |
| 9,911,312 B2 | 3/2018 | Wildman et al. |
| 9,959,743 B2 | 5/2018 | Morgan et al. |
| 10,223,895 B2 | 3/2019 | Hermann et al. |
| 10,475,329 B1 * | 11/2019 | Koester ............... G08B 21/245 |
| 10,818,157 B1 * | 10/2020 | Koester ............... B05B 12/004 |
| 11,348,443 B2 | 5/2022 | Cross et al. |
| 2005/0151641 A1 | 7/2005 | Ulrich et al. |
| 2009/0267776 A1 * | 10/2009 | Glenn .................. G16H 40/20 340/573.1 |
| 2010/0315244 A1 * | 12/2010 | Tokhtuev ............ G08B 21/245 340/603 |
| 2010/0321180 A1 | 12/2010 | Dempsey et al. |
| 2011/0206378 A1 | 8/2011 | Bolling et al. |
| 2012/0112906 A1 | 5/2012 | Borke et al. |
| 2012/0194338 A1 | 8/2012 | Snodgrass |
| 2012/0268277 A1 * | 10/2012 | Best ..................... G08B 21/245 340/573.1 |
| 2013/0253950 A1 | 9/2013 | Vanderpohl, III et al. |
| 2014/0070950 A1 | 3/2014 | Snodgrass |
| 2014/0145915 A1 | 5/2014 | Ribble et al. |
| 2014/0191876 A1 * | 7/2014 | Best ...................... G08B 21/18 340/686.1 |
| 2014/0236611 A1 | 8/2014 | Ribble et al. |
| 2014/0266732 A1 | 9/2014 | Barbeau et al. |
| 2014/0327545 A1 | 11/2014 | Bolling et al. |
| 2014/0375457 A1 | 12/2014 | Diaz |
| 2015/0109442 A1 * | 4/2015 | Derenne ................ H04N 7/185 348/143 |
| 2015/0287182 A1 * | 10/2015 | Herger ................. G06T 11/206 382/128 |
| 2016/0005300 A1 * | 1/2016 | Laufer ..................... H04W 4/33 340/8.1 |
| 2016/0042635 A1 * | 2/2016 | Rosebraugh ....... G09B 19/0076 340/573.1 |
| 2016/0125716 A1 | 5/2016 | Ribble et al. |
| 2016/0136356 A1 | 5/2016 | Moore |
| 2016/0140832 A1 | 5/2016 | Gibson et al. |
| 2016/0213539 A1 | 7/2016 | Gibson et al. |
| 2016/0253897 A1 | 9/2016 | Wildman et al. |
| 2016/0314672 A1 | 10/2016 | Wiggermann et al. |
| 2016/0314683 A1 | 10/2016 | Felch et al. |
| 2016/0350489 A1 | 12/2016 | Ribble et al. |
| 2016/0374847 A1 | 12/2016 | Lachenbruch et al. |
| 2017/0004264 A1 | 1/2017 | Girardeau et al. |
| 2017/0027787 A1 | 2/2017 | Huster et al. |
| 2017/0032656 A1 | 2/2017 | Morgan et al. |
| 2017/0097800 A1 | 4/2017 | Vanderpohl, III |
| 2017/0098366 A1 | 4/2017 | Hood et al. |
| 2017/0112707 A1 | 4/2017 | Huster et al. |
| 2017/0199973 A1 | 7/2017 | Walton et al. |
| 2017/0224561 A1 | 8/2017 | Ribble et al. |
| 2017/0252243 A1 | 9/2017 | Turner et al. |
| 2017/0256155 A1 | 9/2017 | Sengstaken, Jr. |
| 2017/0262593 A1 | 9/2017 | Girardeau et al. |
| 2017/0270766 A1 | 9/2017 | Ribble et al. |
| 2017/0280949 A1 | 10/2017 | Wildman et al. |
| 2017/0287316 A1 | 10/2017 | Wildman et al. |
| 2017/0309155 A1 | 10/2017 | Tallent et al. |
| 2017/0333279 A1 | 11/2017 | Hornbach et al. |
| 2017/0345280 A1 | 11/2017 | Morgan et al. |
| 2017/0358193 A1 | 12/2017 | Ribble et al. |
| 2018/0024202 A1 * | 1/2018 | Erickson ............ G01R 31/3835 340/636.15 |
| 2018/0122214 A1 | 5/2018 | Freedman et al. |
| 2018/0293873 A1 | 10/2018 | Liu et al. |
| 2019/0005801 A1 | 1/2019 | Hermann et al. |
| 2019/0043337 A1 | 2/2019 | Liu et al. |
| 2019/0147731 A1 * | 5/2019 | Herdt .................... A47K 5/1217 340/573.1 |
| 2019/0197873 A1 | 6/2019 | Hermann et al. |
| 2019/0251825 A1 | 8/2019 | Sahud et al. |
| 2019/0259498 A1 | 8/2019 | Sheldon et al. |
| 2020/0302775 A1 | 9/2020 | Liu et al. |
| 2021/0043060 A1 * | 2/2021 | Koester ................ A47K 5/1217 |
| 2021/0166551 A1 | 6/2021 | Cross et al. |
| 2021/0335122 A1 | 10/2021 | Mahmoud |

* cited by examiner

METHODS AND SYSTEMS FOR IMPROVED ACCURACY IN HAND-HYGIENE COMPLIANCE

RELATED APPLICATIONS

This application is a continuation of U.S. Non-Provisional application Ser. No. 17/732,599, which is a continuation of U.S. Non-Provisional application Ser. No. 17/078,436, filed Oct. 23, 2020, now U.S. Pat. No. 11,348,443, which claims priority to and the benefits of U.S. Provisional Application No. 62/924,770, filed on Oct. 23, 2019, all of which are incorporated herein by reference in their entirety.

BACKGROUND OF THE INVENTION

Traditionally, hand hygiene compliance metrics have been obtained through manual audits and observations. Manual audits and observations suffer from a number of deficiencies, such as, for example, observers cannot monitor all hand hygiene stations and all personnel all of the time. In addition, observed compliancy metrics tend to increase when people know that an observer is watching them and tend to decrease when the observer is not present.

A number of companies have been offering technology-based tools that automatically obtain hand-hygiene data used to calculate hygiene compliance metrics without the need for a person to physically observe individuals. These automated electronic hand hygiene compliance monitoring systems receive a signal from the dispenser when the dispenser dispenses a dose of hand cleaner ("a dispense event"). These systems sometimes receive a signal identifying the user that triggers the dispense event. In some cases, a sensor identifies "opportunities" for a user to wash her hands upon entry and/or exit events from a room or other area. The number of opportunities are often compared to the number of dispense events to arrive at a compliance metric. Some of the technology based systems use badges or unique identifiers to identify specific people so that the system can determine whether that particular person complies with the hospital's hand-hygiene policies. In some systems, compliance with the hospital's hand-hygiene policies is not determined on an individual's compliance rate, but rather by floors, wards or overall, i.e. compliance rates for all employees lumped together or for large groups of employees that are lumped together.

The technology-based tools, however, suffer from deficiencies and often result in identification of "false" hand-hygiene opportunities which have a negative effect on the compliance numbers/rates. For example, if an individual triggers 100 hand wash opportunities and washes or sanitizes her hands 60 times, her compliance rate would be 60%, which may be below the target compliance rate. However, if 20 of those 100 hand wash opportunities were "false opportunities", her actual compliance rate would be 75%, which is significantly better than 60%.

The World Health Organization "WHO" has identified five moments when hand hygiene is prescribed: 1) before contact, 2) Before aseptic task, 3) After fluid exposure, 4) After patient contact, and 5) After contact with patient surroundings. Current automated technology-based systems either do not take into effect all of the five moments, or utilize guesswork to attempt to quantify these 5 moments.

SUMMARY

Exemplary embodiments of methods and devices for obtaining more accurate hand hygiene compliance metrics are disclosed herein. An exemplary device or badge for a hygiene compliance system includes a housing; a processor located in the housing; memory in circuit communication with the processor; wireless communication circuitry in circuit communication with the processor; and an additional time input in circuit communication with the processor.

An exemplary methodology for determining a compliance metric includes providing a sensor for detecting an entry event or an exit event into an area, providing a product dispenser and providing a badge having one or more inputs for requesting additional time to obtain a dose of product from the dispenser. The methodology includes a device that includes logic having a selected time period for a person to obtain a dose of product from the product dispenser to qualify for a dispense event. Logic for adding one or more additional time periods to the selected time period if the one or more inputs for requesting additional time are activated is also provided. The exemplary methodology includes logging a dispense event to be used in determining the person's compliance metric if a dose of product is dispensed within one of the selected time period or within the additional time period added to the selected time period.

An exemplary methodology of determining hand hygiene compliance in a hospital as a function of a person's role includes providing a sensor having wireless communication circuitry configured to determine an entry event that is a function of a person's entry into a selected area and transmit a signal indicative of the entry event; obtaining an identifier of the person indicative of the role of the person and determining whether the entry event into the area triggered a hand hygiene opportunity. Determining whether the entry event triggered a hand hygiene opportunity is a function of the role of the person. The methodology includes providing a dispenser for dispensing a fluid, wherein the dispenser has wireless communication circuitry for transmitting a dispense event.

Another exemplary methodology of determining hand hygiene compliance in a hospital as a function of a person's role includes identifying two or more roles, assigning a role to a person, providing a people sensor configured to determine an entry event that is a function of the person's entry into a selected area; wirelessly transmitting a signal indicative of the entry event to a central computer and determining that a person has entered the selected area, and obtaining an identifier of the person that is indicative of the person's role. The methodology further includes providing a sensor configured to determine an exit event that is a function of the person's exit from the selected area and wirelessly transmitting a signal indicative of the exit event to the central computer. The methodology includes determining that a person has exited a selected area, determining whether the entry event into the area triggered a hand hygiene opportunity, and determining whether the exit event from the area triggered a hand hygiene opportunity. Determining whether the entry event and/or the exit event triggered a hand hygiene opportunity is a function of the role of the person. If the role of the person is a first role, an opportunity is triggered each time the person enters or exits the area; and if the role of the person is a second role, an opportunity is not triggered each time the person enters or exits the area.

An exemplary system for determining hand hygiene compliance in a hospital as a function of a person's role includes an entry sensor configured to determine an entry event that is a function of a person's entry into a selected area and an identification device for obtaining an identifier of the person. The exemplary system includes a master station. The master station includes a processor, memory in circuit communication with the processor, and a database stored in the memory. The data base includes a plurality of identifiers identifying a plurality of persons. The data base associates a role with the plurality of identifiers. The system includes logic in the memory for determining whether the entry event into the area triggered a hand hygiene opportunity. Determining whether the entry event triggered a hand hygiene opportunity is a function of the role of the person. A first role triggers a hand hygiene opportunity each time the person enters or exits an area and a second role does not trigger a hand hygiene opportunity each time the person enters or exits an area.

An exemplary methodology for determining hand hygiene opportunities includes obtaining information related to a selected area of a hospital and providing a sensor configured to determine an entry event that is a function of a person's entry into the selected area. The sensor includes wireless communication circuitry for transmitting a signal indicative of the entry event. The methodology includes obtaining a signal that a person has entered the selected area and determining whether the entry event into the area triggered a hand hygiene opportunity. The methodology further includes providing a dispenser for dispensing a product, determining if a dispense event has occurred and determining whether to credit the person with a dispense event. Determining whether the entry event triggered a hand hygiene opportunity is a function of the information related to the selected area. An entry event in a first selected area does not trigger a hand hygiene opportunity and an entry event into a second selected area triggers a hand hygiene event.

Another method of determining hand hygiene opportunities includes identifying two or more roles for hospital workers, providing an asset and obtaining information related to the asset. The methodology further includes providing a sensor configured to determine a location of the asset, determining whether the asset has been in the proximity of a patient and determine that a hospital worker has come in contact with the asset. The methodology further includes determining whether the contact between the hospital worker and the asset triggered a hand hygiene opportunity. Determining whether the contact triggered a hand hygiene opportunity is a function of the information related to the asset and the role of the hospital worker.

Another exemplary methodology for determining hand hygiene opportunities includes providing an asset, obtaining information related to the type of asset, providing a sensor configured to determine a location of the asset, determining whether the asset has been in the proximity of a patient, determining that a hospital worker has come in contact with the asset and determining whether the contact between the hospital worker and the asset triggered a hand hygiene opportunity. Determining whether the contact triggered a hand hygiene opportunity is a function of the information related to the type of asset.

BRIEF DESCRIPTION OF THE DRAWINGS

These and other features and advantages of the present invention will become better understood with regard to the following description and accompanying drawings in which.

DETAILED DESCRIPTION

The Detailed Description describes exemplary embodiments of the invention and is not intended to limit the scope of the claims in any way. Indeed, the invention is broader than and unlimited by the exemplary embodiments, and the terms used in the claims have their full ordinary meaning. Although the exemplary embodiments shown and described herein relate to hospital environments, the inventions disclosed herein may be applicable to other industries, such as, for example, nursing homes, food preparation and processing industries, restaurants, electronics manufacturing and the like. Accordingly, the inventions claimed herein are not limited by the exemplary embodiments, but rather encompass any industry or facility that desires to have a more accurate methods and systems for tracking hand hygiene performance.

Figure 1:
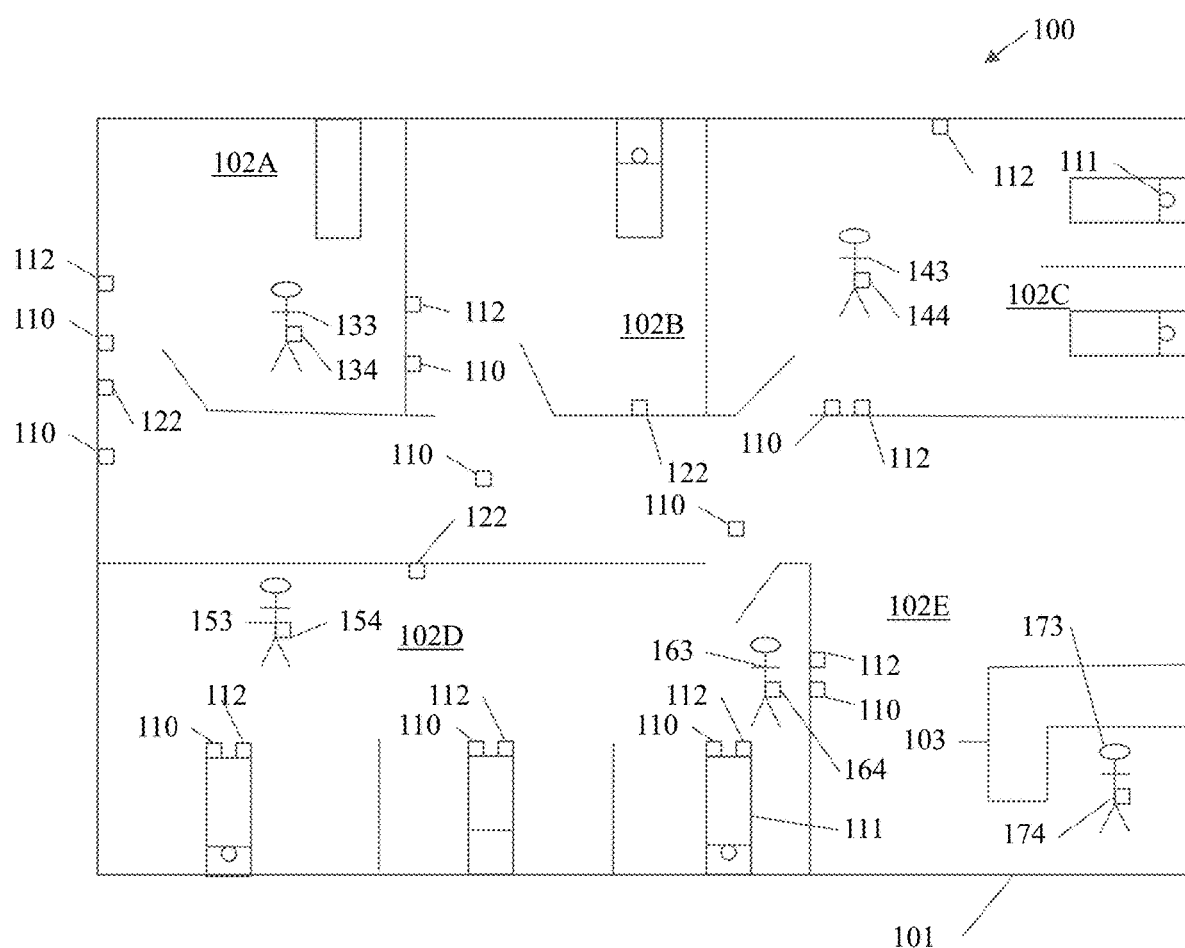
FIG. 1 is a simplified schematic diagram of an exemplary embodiment of an electronic automated monitoring system.

FIG. 1 is a simplified schematic diagram of an exemplary embodiment of an electronic automated monitoring system 100. FIG. 1 illustrates a floor 101 of a hospital. The hospital floor 101 includes a plurality of rooms or areas 102A, 102B, 102C, 102D, 102E. Although the exemplary embodiments described herein relate to hospital environments, the inventive systems and methods of the exemplary embodiments are applicable to any environment where hand hygiene is important, such as, for example, a food preparation environments or other areas wherein whether a person needs to wash or sanitizer their hands, may be a function of the role of that individual.

The automated electronic monitoring system 100 includes a plurality of people sensors 110. People sensors 110 may include any type of sensor such as a motion sensor, an infrared sensor, a photo-emitter/receiver combination, a radio frequency sensor, a beacon sensor, or the like, that may be used to detect the presence of a person. In addition, in some embodiments, people sensors may also be used to detect equipment. Accordingly, the term people sensor is broader than a sensor that senses people. As discussed in more detail below, the detection of equipment and/or people may require or utilize wireless communications devices, such as, for example, badges or tags associated with those people or devices. Exemplary monitors, badges and other equipment that may be used, or modified for use in accordance with the below disclosure, in the innovative systems described herein may be found in PCT Application No. PCT/US20/43438, titled SYSTEMS AND METHODS FOR INCREASED ACCURACY FOR TRACKING HYGIENE COMPLIANCE, which was file on Jul. 24, 2020, and which is incorporated herein by reference in its entirety. Other equipment or portions of equipment that may be used in the exemplary systems, or modified for use in the inventive systems, described herein may be found in U.S. patent application Ser. No. 16/274,597, titled MODULAR PEOPLE COUNTERS, which was filed on Feb. 13, 2019 and which is incorporated herein by reference in its entirety People sensors 110 detect "entries" and/or "exits" into areas of concern, such as, for example, patient rooms or areas 102A, 102B, 102C, 102D, 102E. In some embodiments, the people sensor 110 detects and/or determines the "role" of the person(s) that enter and/or exit the room or area. The detection and/or determination of the role may be made locally at the people sensor 110 (or another device not shown) or maybe made remotely by a central computer (not shown) through the transmission of indicia indicative of the person's role to the central computer.

In some embodiments, the people sensor 110 uses wireless communication circuitry to obtain information indicative of the role of the person. Such information may include for example, a person's role, such as, for example, a doctor, a nurse, a candy striper, a food server, a cleaning person, a technician, a phlebotomist, a physical therapist, a visitor, or the like. In some embodiments, the information may be a unique identifier that is associated with the person and the unique identifier may be used to determine the person's role. In some embodiments, the people sensor 110 receives a signal from a person's badge 144 that is indicative of the persons role. In some embodiments, the people sensor 110 has a sensor (not shown) that detects indicia of a person's role. In some embodiments, the people sensor 110 detects colors, which are correlated to a person's role. For example, the color of the person's clothes may be used to determine the role of the person. In this example, a white outfit may be associated with the role of a doctor, a dark blue outfit may be indicative of a surgeon, a light green outfit may be indicative of a cleaning person, a dark green outfit may be indicative of a food server, etc.

In some embodiment, people sensor 110 includes wireless communication circuitry. The wireless communication circuitry may be short range communication circuitry and/or long range communication circuitry. In some embodiments, the wireless communication circuitry includes a radio frequency receiver and/or transmitter to detect the presence of a person. In some embodiment, the wireless communication circuitry includes a short range wireless receiver and/or transmitter to detect the presence of a person. In some embodiment, the wireless communication circuitry includes a Bluetooth receiver and/or transmitter to detect the presence of a person. In some embodiment, the wireless communication circuitry includes an IR receiver and/or transmitter to detect the presence of a person. In some embodiments, short range communication circuitry is used to determine the presence of a person and long range communication circuitry may be used to communicate with a central computer.

Preferably, the system includes a plurality of identification devices, such as, for example, identification devices 134, 144, 154, 164, 174, which may also be referred to herein as electronic identifiers. The identification devices may be, for example, a badge that is carried or worn by the user and the badge includes wireless communication circuitry that communicates information indicative of the person and/or the role of the person. In some embodiments, the identification devices 134, 144, 154, 164, 174, are a personal data device, such as, for example, a smart phone that is carried by the user and detected by the people sensor 110. In some embodiments, the identification devices 134, 144, 154, 164, 174, are microchips that are embedded in the person and/or equipment.

The term "badge" as used herein is not limited to traditional badges worn by a person, but rather includes any device that is configured to provide information relating to the person and/or the role of the person, such as, for example, a bracelet, a card, a necklace, Google glasses, a tag, a bar code, a smart phone, and the like. The term badge may be used generically to refer to identification devices. In some embodiments, a biometric sensor (not shown) is included in people counter 110 and is used to identify the person and/or role of the person. The biometric sensor (not shown) may include, for example, optics for facial recognition, vein recognition, retina recognition, finger print recognition or circuitry and/or software required for any other type of biometric data. In such embodiments, an identification device carried by the person may not be required.

In some embedment's the identification devices 134, 144, 154, 164, 174, are passive devices that are activated by the people sensor 110. For example, the people sensor 110 may transmit a signal that when received by the identification devices 134, 144, 154, 164, 174, causes the identification devices 134, 144, 154, 164, 174, to broadcast information or link with the people sensor 110 to provide the requested information or indicate the presence of one or more people or equipment.

In some embodiments the identification device 134, 144, 154, 164, 174 is an active device that broadcasts its information periodically, such as, for example, every 0.3 seconds and the signal is picked up by a people counter 110. In some embodiments, the transmitted signal contains all the desired information or data. In some embodiments, identification device 134, 144, 154, 164, 174, contains both passive circuitry that responds to a signal from the people sensor 110, and active circuitry that produces a periodic signal that is received by the people sensor 110. In some embodiments, when the people sensor 110 receives a signal from the identification device 134, 144, 154, 164, 174, the people sensor 110 responds with a communication request for additional information from the identification device 134, 144, 154, 164, 174. In some embodiments, passive devices receives a signal and wakes up an active device to transmit data or information.

In some embodiments, people sensor 110 may include an optical system, such as, for example, a camera and the role of the person may be obtained through use of analytical software that analyses a captured image(s) to electronically identify what task the person is completing. Similarly, the optical system may be used to electronically identify dispense events from a dispenser and/or to whom the dispenser has dispensed the product. Thus, in this exemplary embodiment, irrespective of the persons actual title or primary job, for the purpose of determining whether an action triggered an opportunity, the "task" performed determines whether an opportunity has occurred. Thus, in some embodiments the "role" is defined by the task completed not the title of the person that normally performs the task.

The role of the person may be determined locally by the people sensor 110 (or other local device (not shown)), or remotely through use of information transmitted by the people sensor 110 to a remote computing device (not shown) that determines the role of the person at a location remote from the people sensor 110. In the latter case, in some embodiments, people sensor 110 may transmit information, such as, for example, a unique identifier that identifies the person to the central computer. A lookup table may be provided in the remote computing device that cross-references the unique identifier with the role of that person.

The signal that includes data on information indicative of the identification of a person and/or the role of the person may be sent directly to the remote computer (not shown)

from the people sensor 110. In some embodiments, the signal may be sent to an intermediate device, such as, for example, a dispenser 112 or a gateway (not shown), which sends or relays the data or information to the remote computer. The people sensor 110 may send one or more of an "entry" signal, an "exit" signal, an entry time stamp, an exit time stamp, one or more signals indicative of the identify of a person and/or the role of the person, or the like. In some embodiments, the "role" of the user, the "entry" signal and/or "exit" signal is sent to the remote computer and the remote computer stamps the time entry upon receipt of the communication signal.

System 100 includes a plurality of dispensers 112. Dispenser 112 is used to dispense a product, such as, for example, hand sanitizer or soap. Dispenser 112 may be a manual dispenser or a touch-free electronic sensor. Dispenser 112 includes circuitry to detect the dispensation of fluid, i.e. a "dispense event" and to send a signal back to a remote computer, the people counter 110 or identification device. The signal may include one or more of a dispense event, a "time stamp", an identifier identifying a person and/or role of a person, a location of the dispenser, and the like. The signal may be sent directly to the remote computer (not shown) or may be sent through one or more intermediary devices, such as, for example, the people sensors 110 or a gateway device (not shown). Optionally, the remote computer that receives the dispense events may log a time of receipt as the time stamp. Exemplary dispensers 112 and associated wireless communication modules may be found in U.S. Pat. No. 9,633,545 titled HYGIENE COMPLIANCE MODULE and U.S. Pat. No. 10,373,477 titled HYGIENE COMPLIANCE MODULES FOR DISPENSERS, DISPENSERS AND COMPLIANCE MONITORING SYSTEMS, which are incorporated herein by reference in their entirety.

In this exemplary embodiment, people sensors 110 are located near the entrances to areas and/or near exits to the areas. The areas may be a confined area, such as, for example a room, or the "areas" may be a portion of a room proximate the people sensor 110. In some embodiments, people sensors are also located periodically in hallways, corridors and the like. Accordingly, in this exemplary embodiment, when a person enters or exits a room 102A, 102B, 102C, 102D, approaches or leaves a patient bed 111, or enters and leaves the nurse station 102E, their presence is detected. In some embodiments, people sensor 110 can detect the direction of travel of the person. Dispensers 112 are preferably located at strategic locations that are intended to trigger use dispenser usage and that readily enable a person to comply with a desired hygiene compliance program. In this exemplary embodiment, dispensers 112 are located near nursing station 103, near doorways into the rooms/areas 102A, 102B, 102C, 102D and near patient beds 111.

As described above, electronic identifier 134, 144, 154, 164, 174 may be referred to as badges. In some embodiments, the electronic identifier 134, 144, 154, 164, 174 transmits a unique ID so that the remote computer may determine which person assigned to electronic identifier 134, 144, 154, 164, 174 triggered an entry/exit event(s) or a dispense event.

Compliance rates or compliance metrics are calculated by determining the number of opportunities that have been triggered by a person divided by the number of dispense events associated to that person. In some exemplary embodiments, the role of the person, may be used as a factor in determining a compliance metric or compliance ratio. In some embodiments, the compliance metric or rate is adjusted after it is calculated based on the person's role. For example, if a person has a role that typically negates a set % of entry or exit events from triggering an opportunity, the compliance rate may be increased by a set % for persons having that role Preferably, the number of opportunities or dispense events are adjusted based on the person's role, prior to calculating the compliance rate.

The terms compliance metric and compliance ratio may also be referred to as a compliance rate. Thus, a more accurate "compliance metric or compliance ratio" for a person may be calculated by taking into consideration a person's role. For example, each time a person having a "role" of a "doctor" enters or exits room, an opportunity to sanitizer or wash their hands may occur. However, with respect to a person having a "role" of a janitorial staff member, all entries or exits a room may not trigger an opportunity to sanitizer or wash their hands, particularly, if they do so multiple times within the set period of time. Similarly, person performing the role of a food server, should not have an opportunity to wash or sanitizer their hands logged or counted in their metric when the person enters the room carrying a tray of food, because the person cannot wash or sanitizer her hands at that point in time, however when the person performing the role of the food server leaves the room, an opportunity to wash or sanitizer her hands should be recorded and counted in their metric. In addition, if a doctor and a group of residents enters a patient's room, the entry event should not trigger opportunities to wash or sanitize one's hands for each of the residents and the doctor. Accordingly, based on the role of the individual, an entry event or an exit event, or multiple entry events and exit events within certain time periods, may not trigger opportunities to wash or sanitize their hands that are used to compute their compliance rate or metric. This may be accomplished by detecting a doctor and two or more residents within a set area. In such a case, in one embodiment two opportunities would be recorded for the group. In some embodiments, the number of doctors and the number of residence divided by X is used for opportunities, where X is a function of the total number of people.

In the exemplary embodiment shown in FIG. 1, person 133 is caring an electronic identifier 134. Electronic identifier 134 includes information that is indicative of the role of person 133. In this exemplary embodiment person 133 is a nurse. The electronic identifier 134 may include the indicia, or may provide a unique ID that may be used at a remote location to determine that person 134 was a nurse. As disclosed above, in some embodiments the electronic identifier 134 may be replaced or used in addition to other means for determining the role the person, such as for example, clothing color, biometrics and the like.

Because person 133 is a nurse, the nurse may trigger an "opportunity" to wash her hands each time she enters or exits the room. Thus, when people sensor 110 detects person 133 entering or exiting the room 102A an entry event or exit event is logged in the system. For each entry event and each exit event, an "opportunity" is identified and is used to determine person 133's compliance metric or compliance rate. Preferably the time of entry or exit is also logged in the system. When person 133 users dispenser 112, which may be a soap dispenser or a sanitizer dispenser, a dispense event is logged and associated with person 133.

In this exemplary embodiment, person 143 is associated with electronic identifier 144. Person 143 may have the role of food server. Accordingly when person 143 enters and exits a room 102C, the entry event is determined by people sensor 110 and logged and the exit event is determined by people sensor 110 and logged. However, only one "opportunity" to wash or sanitize their hands is assigned to the person in this role as it is assumed that the person 143 is most likely either bringing food to the patient 111 or taking empty plates and trays from the patient 111 and, accordingly, likely has their hands full either when entering or when exiting the room. If person 143 users dispenser 112, the dispense event is logged in associated with person 143. In this exemplary embodiment, person 143 entered the room and was detected by people sensor, logging an entry event, and person 143 exited the room and was detected by people sensor 110, logging an exit event, and obtained a dose of hand sanitizer logging a dispense event. In prior art systems, person 143 would have a compliance rate of 50%, two entry/exit events triggering two opportunities divided by one dispense event. In this case, however, because person 143's role is a food service worker, only one opportunity is counted in her metric for the entry even and the exit event, making her compliance rate 100%. The assigned opportunities and dispense events may be used to determine the compliance metric. Thus, in some embodiments the number of "opportunities" associated with a person's compliance metric may be reduced (or, in some cases increased) as a function of a person's role or the duties being performed. Thus, not all entry events and exit events trigger a separate or single opportunity that is counted in determining the compliance rate for selected individuals.

In this exemplary embodiment, person 153 is associate with electronic identifier 154. Person 153, is in a janitorial role, and may be coming in and out of the room 102D in performing the janitorial services. In coming in and out of the room person 154 is detected by people sensor 110 and each time person 153 enters the room, an entry event is logged. Each time the person 153 exits the room an exit event is logged. As described above, not all of these entry events and exit events should be counted as an "opportunity" for person 153 to wash or sanitize her hands in arriving at her compliance rate. In some embodiments, only one opportunity is logged irrespective of how and times person 153 enters or exits the room. In some embodiments, only one opportunity is logged for person 153 per room no matter how many times person 153 enters and exits the room. In some embodiments, additional opportunities will be logged if person 153 enters a different room between entries and exits of the first room. In some embodiments, a timing function is associated with person 153, and multiple entry and/or exit events that occur within a selected time period are logged as only one opportunity to wash or sanitize their hands. If the time elapsed is over the set time period, another opportunity to wash or sanitize their hands will be logged or entered upon the next entry or exit of a room and counted in person 153's compliance metric.

In this exemplary embodiment, person 163 is associate with electronic identifier 164 and has the role of a visitor. In some embodiments a person 163 having a visitor role does not have electronic identifier, and the system determines that any person that does not have electronic identifier is visitor. In this embodiment when the visitor 164 enters a room people sensor 110 determines that a visitor has entered the room and determines that an opportunity for that visitor has occurred so that the visitor 164 should wash or sanitizer her hands with dispenser 112 prior to coming in contact with patient 111. In some embodiments, exiting the room will not trigger an opportunity for person 164 when they're leaving.

In this exemplary embodiment, person 173 has electronic identifier 174 associated therewith and person 173 has the role of an aid. Therefore person 173 may be entering and exiting rooms 110 to bring or retrieve items, such as, for example, IV poles, heart monitors, or other medical equipment, and such activity while triggering both an entry event and exit event may be determined to count for less opportunities being logged or used in the compliance metric than the total number of entry and exit events. For example, an entry event and an exit event may only trigger one opportunity instead of the normal two opportunities. As described above, in some embodiments, a timing function may be used and person 173 may result in having opportunities logged or counted that are a function of an entry event and/or an exit event and time. For example, person 173 may enter a room and log an entry event. A timer may be started. Each time person 173 enters and exits the room an entry event and an exit event is logged, however, only one opportunity is logged and counted toward the compliance metric. After a set time expires, the next entry event or exit event causes another opportunity to be logged.

Exemplary methodologies for improving hand hygiene metrics are disclosed herein. Although the blocks and methodologies are shown and described in a certain order, the exemplary steps may be completed in different orders, different combinations, with additional steps and/or without certain steps, all of which are included in the scope of the present invention. In addition, additional steps or determinations may be included in other embodiments or borrowed from other embodiments. Similarly, in some embodiments, some steps or determinations may be eliminated or combined with other steps or determinations. In addition, various portions of selected exemplary embodiments may be combined with all or portions of one or more other exemplary embodiments.

Figure 2:
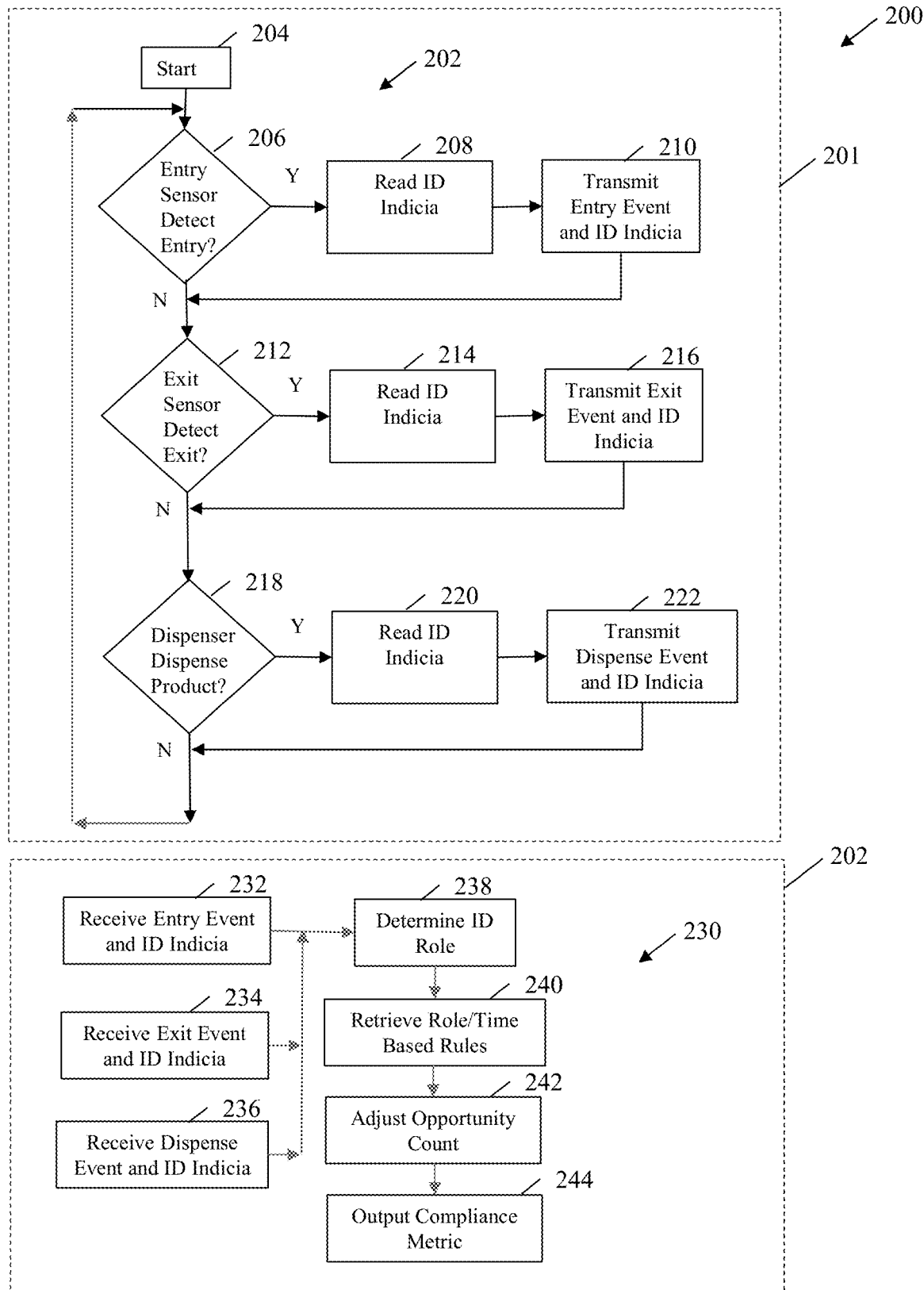
FIG. 2 is an exemplary methodology of obtaining more accurate hand hygiene compliance metrics.

FIG. 2 illustrates an exemplary methodology for an improved hand hygiene compliance system 200. The exemplary methodology begins at block 204. At block 206 a determination is made as to whether an entry sensor detected entry to a room or area. The entry may be detected by, for example, a people counter as described above. If no entry has been detected the methodology flows to block 212. If an entry has been detected, identification indicia of the person or asset entering the room is read at block 208. The indicia may be obtained through any of the manners described above, such as, for example, reading a transmission from a badge. After the identification indicia is obtained, the system transmits an entry event and identification indicia to a central computer at block 210. In some embodiments, a central computer is not used and relevant calculations and number of opportunities occurring are calculated locally. In some embodiments, the entry event and/or identification indicia are stored in the badge and transmitted at a later time. In some embodiments, the entry event and/or identification indicia are stored in the people counter or entry sensor and transmitted at a later time. The exemplary methodology flows to block 212.

At block 212 a determination is made as to whether an exit sensor detected a person exiting the room or area. The exit may be detected by, for example, a people counter as described above. If no exit has been detected the methodology flows to block 218. If an exit event has been detected, identification indicia of the person exiting the room is read at block 214. The indicia may be obtained through any of the manners described above, such as, for example, reading a transmission from a badge. After the identification indicia is obtained, the system transmits an entry event and identification indicia to a central computer at block 216. In some embodiments, a central computer is not used and relevant calculations and number of opportunities occurring are calculated locally. In some embodiments, the exit event and/or identification indicia are stored in the badge. In some embodiments, the exit event and/or identification indicia are stored in the people counter or exit sensor. The exemplary methodology flows to bloc 218. In some embodiments, if only one entry event has occurred, the system may assume the identification indicia of the person triggering the exit event is the same as that that triggered the entry event.

At block 218 a determination is made as to whether a dispenser has dispensed product. The dispense may be detected by, for example, a smart dispenser or a dispenser having a compliance module as described above. If no dispense has been detected the methodology flows back to block 206. If a dispense event has been detected, identification indicia of the person that receive the dose of product is read at block 220. The indicia may be obtained through any of the manners described above, such as, for example, reading a transmission from a badge. After the identification indicia is obtained, the system transmits the dispense event and identification indicia to a central computer at block 222. In some embodiments, a central computer is not used and relevant calculations and number of opportunities occurring are calculated locally. In some embodiments, the dispense event and/or identification indicia are stored in the dispenser. In some embodiments, the exit event and/or identification indicia are stored in the people counter or entry sensor. The exemplary methodology flows back to block 216.

Entry events and identification indicia are received at block 232. Exit events and identification indicia are received at block 234. Dispense events and identification indicia are received at block 232. Roles of the individuals triggering entry events, exit events and dispense events are determined at block 238. A database of role and time based rules may be retrieved at block 240. At block 242, opportunity counts are adjusted as a function of the person's at block 244. Based on a person's role, the number of opportunities may be increased, the number of opportunities may be decreased, or the number of opportunities may stay the same. At block 244, one or more compliance metrics are outputted for the individual or group of individuals. This may be done locally or at a remote computer (not shown).

Figure 3:
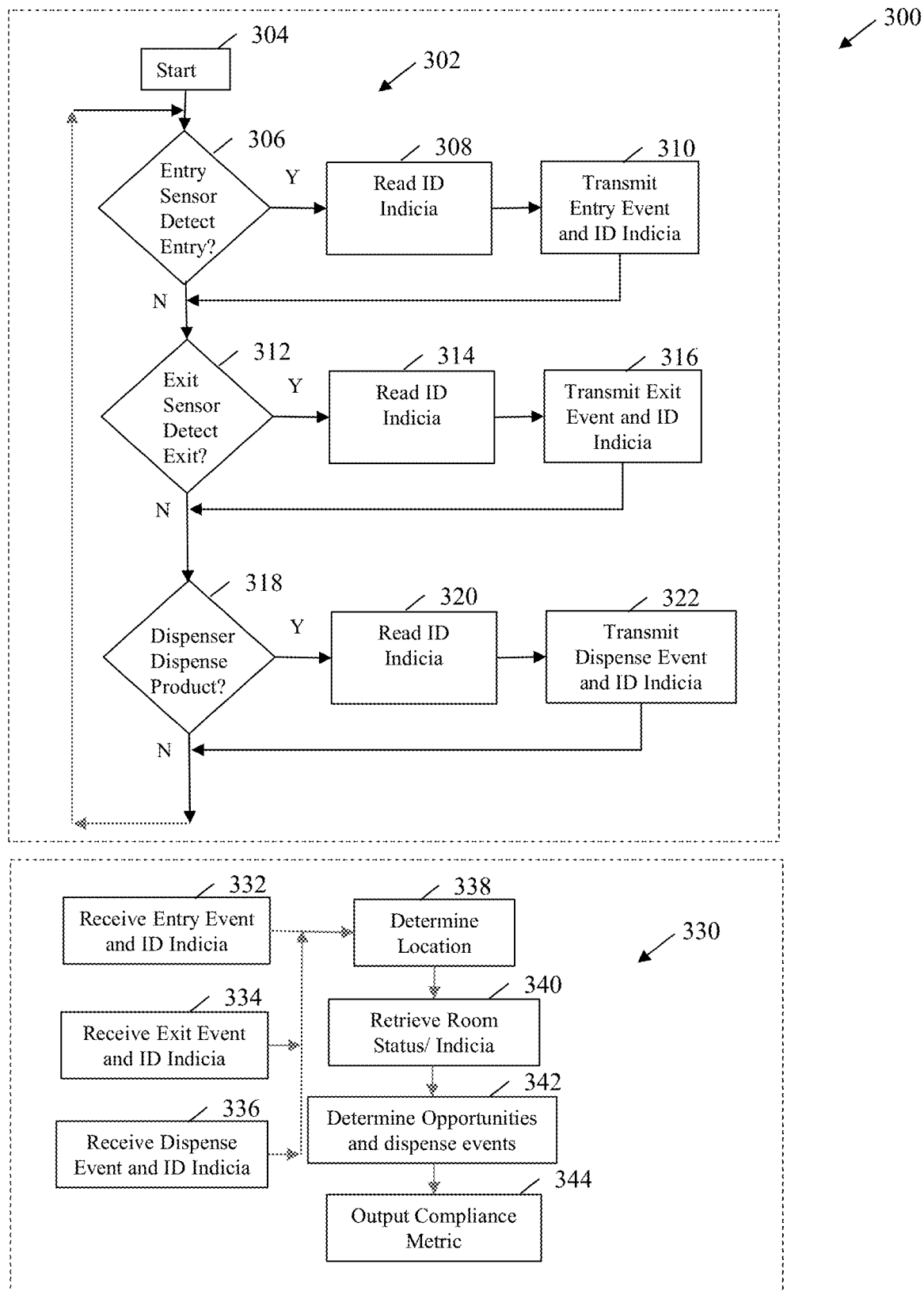
FIG. 3 is another exemplary methodology of obtaining more accurate hand hygiene compliance metrics.

FIG. 3 illustrates an exemplary methodology for an improved hand hygiene compliance system 300. The exemplary methodology begins at block 304. At block 306 a determination is made as to whether an entry sensor detected entry to a room or area. The entry may be detected by, for example, a people counter as described above. If no entry has been detected the methodology flows to block 312. If an entry has been detected, identification indicia of the person entering the room is read at block 308. The indicia may be obtained through any manner, such as, for example, reading a transmission from a badge. After the identification indicia is obtained, the system transmits an entry event and identification indicia to a central computer at block 310. In some embodiments, a central computer is not us used and relevant calculations and number of opportunities occurring are calculated locally. In some embodiments, the entry event and/or identification indicia are stored in the badge and transmitted later. In some embodiments, the entry event and/or identification indicia are stored in the people counter or entry sensor and transmitted at a later time. The exemplary methodology flows to block 312.

At block 312 a determination is made as to whether an exit sensor detected a person exiting the room or area. The exit may be detected by, for example, a people counter as described above. If no exit has been detected the methodology flows to block 318. If an exit has been detected, identification indicia of the person exiting the room is read at block 314. The indicia may be obtained through any manner, such as, for example, reading a transmission from a badge. After the identification indicia is obtained, the system transmits an exit event and identification indicia to a central computer at block 316. In some embodiments, a central computer is not us used and relevant calculations and number of opportunities occurring are calculated locally. In some embodiments, the exit event and/or identification indicia are stored in the badge and transmitted at a later time. In some embodiments, the exit event and/or identification indicia are stored in the people counter or exit sensor and transmitted at a later time. The exemplary methodology flows to block 318.

At block 318 a determination is made as to whether a dispenser has dispensed product. The dispense may be detected by, for example, a smart dispenser or a dispenser having a compliance module as described above. If no dispense has been detected the methodology flows back to block 306. If a dispense event has been detected, identification indicia of the person that receive the dose of product is read at block 320. The indicia may be obtained through any manner, such as, for example, reading a transmission from a badge. After the identification indicia is obtained, the system transmits the dispense event and identification indicia to a central computer at block 322. In some embodiments, a central computer is not us used and relevant calculations and number of opportunities occurring are calculated locally. In some embodiments, the dispense event and/or identification indicia are stored in the dispenser and transmitted at a later time. In some embodiments, the exit event and/or identification indicia are stored in the people counter or entry sensor and transmitted at a later time. The exemplary methodology flows back to block 306.

Entry events and identification indicia are received at block 332. Exit events and identification indicia are received at block 334. Dispense events and identification indicia are received at block 336. The location of triggering entry events, exit events and any dispense events are determined at block 338. In addition, time stamps may be obtained for the entry events, exit events and dispense events.

In this exemplary embodiment, the room status is retrieved at block 340. The room status may be, for example, single patient occupancy, double patient occupancy, critical care, neonatal care, empty ready for occupancy, empty just vacated, whether the patient is a "contact precautions" patient, such as, for example, a patient that has C-Difficile, and the like. At block 342, opportunity counts and dispense events for the individuals that are a function of the room status are determined and at block 344. At block 344 one or more compliance metrics are outputted for the individual or group of individuals. The status of the room may be retrieved from, for example, the electronic medical records systems.

In this exemplary embodiment, if the room status is "empty ready for occupancy" and a person with a health care provider role enters or exits the room, no "opportunity" to wash or sanitize one's hands will be logged. If the room status is "empty just vacated", if a doctor enters the room and exits the room, one opportunity may be logged and counted in the compliance metric, one for both the entry and the exit. In some embodiments two opportunities may be logged.

In another example, if a health care worker enters into a room that has a contact precautions status based on, for example, a patient with C-diff, an opportunity will be logged for the entry event and a second will be logged for the exit event. If the healthcare worker obtains a dose of soap upon entering the room, a dispense event will be logged and used in the determination of the compliance metric. If the healthcare worker obtains a dose of sanitizer, the dispense event will be logged, however it will not be used in the determination of the compliance metric, because a dose of sanitizer is not effective efficacious against C-diff. Accordingly, in this exemplary embodiment, the compliance metric or compliance rate would be 50% (# of counted dispense events/# of opportunities*100%).

In addition, in some embodiments, depending on the status of the room, additional opportunities may be triggered as a function of time spent in the room or area. For example, if at block 340 it is determined that the person has an infections disease, an opportunity is logged or counted for each entry event, each exit event, and an additional opportunity is logged for every X minutes. In this exemplary embodiment, X may be, for example, 10 minutes, 5 minutes, 3 minutes or the like. Thus, if X is 5 minutes, a person entering the room and staying for 10 minutes would have four (4) opportunities logged to be counted in their compliance metric, one for the entry event, two for the two expired time periods and one for the exit event.

Thus, in some embodiments, the retrieved room status/indicia may result in increasing the number of opportunities used in the person's compliance metric. However, in some embodiments, the retrieved room status/indicia may result in decreasing the number of opportunities used in the person's compliance metric.

In some embodiments, both the roles of the individual and the status of the room may be used to adjust the opportunity analysis. In one exemplary embodiment, the room status is "empty just vacated" and a doctor both enters the room and exits the room. Because the room status is empty just vacated, the room may still be contaminated, however there is no patient. Accordingly, only one opportunity will be logged for the doctor to have washed or sanitized her hand, one for the entry and one for the exit. If a janitorial staff enters and exits the same room, only one opportunity for the janitorial staff member to wash or sanitize her hands is logged upon the exiting of the room. However, if that janitorial staff repeatedly enters and exits the room, one opportunity is logged upon the last exit over a selected period of time, as it may be assumed the janitorial staff was cleaning the room. If the room has an occupied status, a doctor may log two opportunities upon entry and exit. Similarly, a janitorial staff may log two opportunities if the room has an occupied status.

Figure 4:
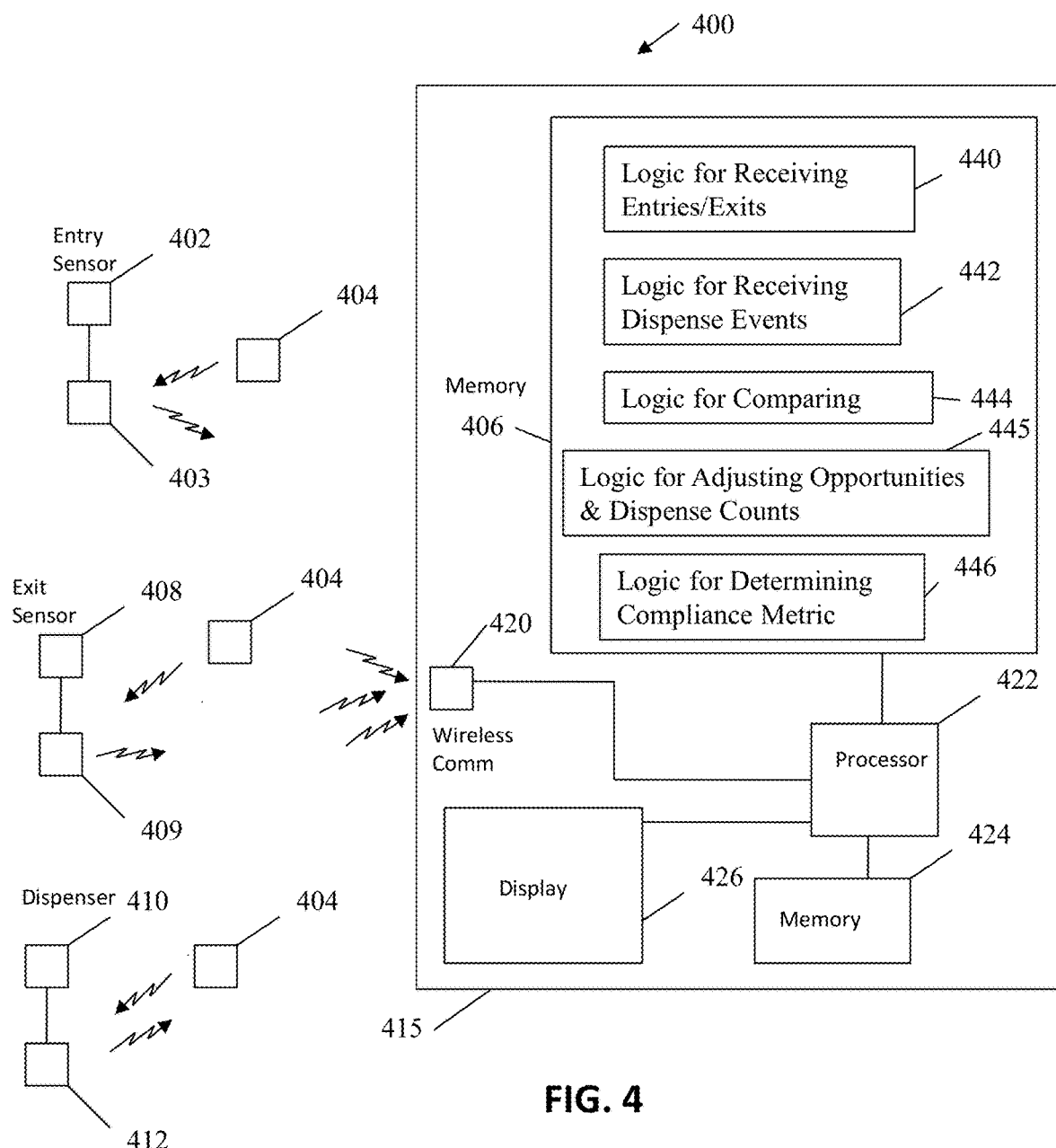
FIG. 4 is an exemplary embodiment of a system for obtaining more accurate hand hygiene compliance metrics.

FIG. 4 is a simplified schematic diagram 400 for a system for performing the exemplary methodologies herein. "Circuit communication" as used herein indicates a communicative relationship between devices. Direct electrical, electromagnetic and optical connections and indirect electrical, electromagnetic and optical connections are examples of circuit communication. Two devices are in circuit communication if a signal from one is received by the other, regardless of whether the signal is modified by some other device. For example, two devices separated by one or more of the following—amplifiers, filters, transformers, optoisolators, digital or analog buffers, analog integrators, other electronic circuitry, fiber optic transceivers or satellites—are in circuit communication if a signal from one is communicated to the other, even though the signal is modified by the intermediate device(s). As another example, an electromagnetic sensor is in circuit communication with a signal if it receives electromagnetic radiation from the signal. As a final example, two devices not directly connected to each other, but both capable of interfacing with a third device, such as, for example, a CPU, are in circuit communication.

System 400 includes a plurality of entry sensors 402 (only one is shown for simplicity). Entry sensor 402 includes a sensor for detecting the entrance of one or more persons or assets to a room or area. In addition, entry sensor 402 includes wireless communication circuitry 403 for communicating with a plurality of badges 404 (only one is shown for simplicity) and with a remote processing unit 415. Badge 404 may be on a person or an asset. Wireless communication circuitry may have short range communication circuitry and/or long range wireless communication circuitry.

Similarly, system 400 includes a plurality of exit sensors 408 (only one is shown for simplicity) that include a sensor for detecting one or more persons or assets exiting a room or area. Exit sensors 408 also include wireless communication circuitry 409 for communicating with a badge 404 and with a remote processing unit 415. Wireless communication circuitry may have short range communication circuitry and/or long range wireless communication circuitry. Entry sensors 402 and 408 may be the same sensor.

Exemplary entry sensors and exit sensors, which may be referred to herein as people sensors, are described above and in the references incorporated herein. In some embodiments, the exit and entry sensors 402, 408 do not need to communicate with badges 404 and include sensors for determining one or more characteristics of the person(s) being sensed, such as, for example, a biometric sensor or color sensor, some of which are discussed in more detail above.

A plurality of dispensers 410 (only one is shown for simplicity) are included in the system. Preferably, the dispensers 410 include a sensor for detecting one or more persons receiving doses of product therefrom. In some embodiments dispensers 410 also include wireless communication circuitry for communicating with a badge 404 and with a remote processing unit 415. Wireless communication circuitry may have short range communication circuitry and/or long range wireless communication circuitry.

Remote processing unit 415 includes a processor, wireless communication circuitry in circuit communications with the processor 422 and a display 426 in circuit communications with the processor 422. In addition, an input device 424, such as, for example, a keyboard, is in circuit communication with processor 422. Memory 406 is also in circuit communication with processor 422.

Memory 406 may be any type of memory such as for example, Random Access Memory (RAM); Read Only Memory (ROM); programmable read-only memory (PROM), electrically programmable read-only memory (EPROM), electrically erasable programmable read-only memory (EEPROM), magnetic disk or tape, optically readable mediums including CD-ROM and DVD-ROM, or the like, or combinations of different types of memory. In some embodiments, the memory 406 is separate from the processor 422, and in some embodiments, the memory 406 resides on or within processor 422.

System 400 includes logic for performing the exemplary methodologies described in more detail herein. Located in memory 406 is logic 440 for receiving data indicative of opportunities, e.g. one or more of: entry events, exit events, badge numbers, data indicative of the person entering or exiting, data indicative of the role of the person, time, location, and date. In addition, located in memory 406 is logic 442 for receiving data indicative of dispense events from the dispenser 410. Preferably, the data for the dispense event includes what type of product is being dispensed, e.g.

soap or sanitizer. In addition, in some embodiments, one or more of: the locations of the dispense events, a badge number, data indicative of the identity of the person receiving the dose of product, the role of the person receiving the dose of product, time of dispense may also transmitted from the dispensers.

Memory 406 includes logic 444, which may include logic for determining roles, logic for comparing one or more: entry times, exit times and dispense event times; logic for retrieving room status designations; logic for role identification and role and/or time based rules.

In addition, memory 406 includes logic 445 for adjusting opportunities. The opportunities may be adjusted downward or upward. The adjustment to the opportunities, may include, for example, reducing the number of opportunities based on a person's role, reducing the number of opportunities as a function of time in an area and the persons role, reducing the number of opportunities as a function of the activity performed by the person, reducing the number of opportunities as a function of the status of the room or area, and the like. In some embodiments, the number of opportunities are increased as a function of the person's role. In some embodiments, the number of opportunities are increased as a function of the status of the room such as, for example, a room with a person having an infectious disease, a room with a C'diff patient, a room with a virus, such as, Covid and the like.

Some exemplary electronic monitoring systems disclosed herein utilize timing rules in combination with entry events and exit events for to look "back" in time and look "forward" in time for dispense events that that occur within a period of time in which the "opportunity" triggered by the entry/exit events occurred. If a set period of time elapses between the entry/exit event that triggers an opportunity and the dispense event, the dispense event is logged, but it is not used or counted in the calculation of the compliance metric or compliance rate. So, for example, when a doctor walks into a patient room, she triggers an opportunity and has a set period of time, e.g. 20 seconds, to obtain a dose of product from a dispenser, a "dispense event", to be in compliance with the establishment's, e.g. hospital's, compliance policies. However, if the doctor stops to talk the mother of the patient, and does not cause the dispenser to dispense product until 30 seconds have elapsed, the doctor is not credited with the dispense event and their compliance metric or compliance rate is lower than it should be.

Figure 5:
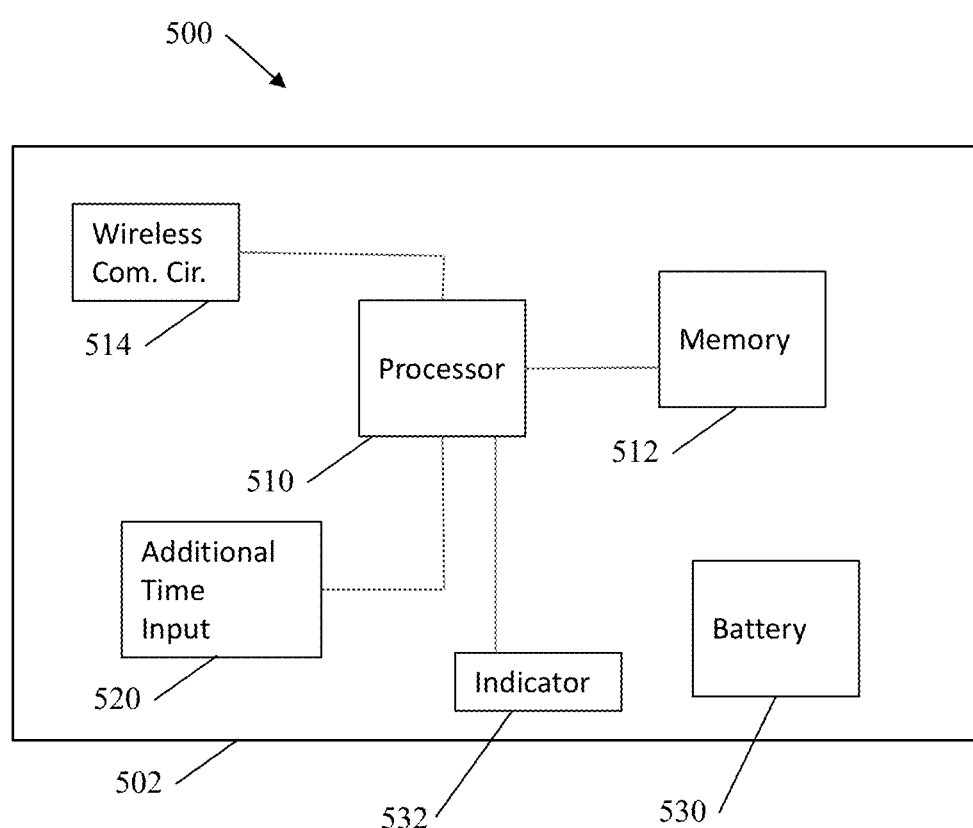
FIG. 5 is a simplified schematic diagram of an exemplary badge having an additional time input.

FIG. 5 is a simplified schematic diagram of an exemplary embodiment of a badge 500. Badge 500 includes a processor 510 in circuit communications with memory 512, a power source 530, an optional indicator 532, additional time input 520, and wireless communication circuitry 514. A power source 530 is provided to power the circuitry as required.

The term "badge" as used herein may be a stand-alone device such as, for example, a conventional badge, a tag, a bracelet, the like or may be integrated in another device, such as, for example, a smart phone, tablet, iPad, or the like. In some embodiments, the integrated device may include application software so that the device performs any of the required functions described herein.

Processor 510 may be any type of processor, such as, for example, a microprocessor or microcontroller, discrete logic, such as an application specific integrated circuit (ASIC), other programmed logic device or the like.

Processor 510 is in circuit communication with memory 512. Memory 512 may be any type of memory, such as, for example, Random Access Memory (RAM); Read Only Memory (ROM); programmable read-only memory (PROM), electrically programmable read-only memory (EPROM), electrically erasable programmable read-only memory (EEPROM), flash, magnetic disk or tape, optically readable mediums including CD-ROM and DVD-ROM, or the like, or combinations of different types of memory. In some embodiments, the memory 512 is separate from the processor 510, and in some embodiments, the memory 512 resides on or within processor 510.

Wireless communication circuitry 514 may be, for example, wireless circuitry for transmitting/receiving communications, such as for example, wireless RF circuitry, BlueTooth® circuitry, ANT® circuitry, or the like. In some embodiments, the circuitry is near field communications.

Power source 530, may be, for example, one or more batteries. Optional indicator 532 may be, for example, one or more LEDs, a display, such as, for example, a liquid crystal display, a graphical display, or the like.

Additional time input 520 may be any type of input, such as, for example, a button, a switch, a sensor, a microphone, a touch screen, or the like. Additional time input is configured to allow the user to request additional time to perform a hand-hygiene compliance task, e.g. obtain a dose of soap or sanitizer. In some embodiments, additional time input may be a "freeze" input, that freezes the timer until the freeze input is released or turned off.

As described in detail herein, the compliance monitoring systems often use timing rules to indicated if a healthcare worker wearing a badge was "compliant", i.e. washed or sanitized their hands within an allotted period of time from triggering an "opportunity" to perform a hand hygiene function. In some embodiments, the compliance system software looks "behind" to see if the healthcare worker washed or sanitized their hands within a selected period of time before triggering the opportunity, and in some cases the compliance system software looks "ahead" to see if the healthcare worker washes or sanitizes her hands after triggering the opportunity.

While a healthcare worker is performing her duties, she triggers an opportunity to complete a hand hygiene event that must be completed in a set time, however, in some circumstances, she may not be able to complete a hand hygiene event in the allotted time. Badge 500 includes "additional time" input 520, which can be activated by the healthcare worker. The additional time input 520 provides additional time for the healthcare worker to complete a hand-hygiene event and have that hand hygiene event used in determination of her compliance metric. In some embodiments, activating the additional time input 520 causes a signal to be sent to a software processing engine in a central computer to adjust the compliance timing rule for that individual.

In some embodiments, the additional time input 520 adds a set amount of time, such as, for example, 10 seconds, 15 seconds, 30 seconds, 45 seconds, 60 seconds, or the like. In some exemplary embodiments, the additional time input 520 adds a set amount time based on the healthcare worker's role. For example, a doctor may get less time added than a food server does when activating the additional time input. In some exemplary embodiments, the additional time input 520 adds a set amount of time based upon a task or workflow being completed. In some embodiments, the first time a healthcare worker activates the additional time input 520, they are allotted a first amount of time and the second time the additional time input 520 is activated, within a set time period, the healthcare worker is allotted a second amount of time. In some embodiments, the second amount of allotted time is less than the first amount of allotted time. In some embodiments, there are more than one "additional time" inputs which allows for different amounts of time to be added to the compliance timing rules. In this exemplary embodiment, a healthcare worker, or other worker that needs to comply with a compliance monitoring system, can activate different additional time inputs based upon the different tasks or workflows being performed. In some embodiments, two or more additional time inputs may be activated simultaneously, or sequentially, to request different amounts of time to be added to the timing rules.

In addition, in some embodiments, the system tracks the number of times a healthcare activates the additional time input 520. If the number of times exceeds a set threshold, an alert may be activated. In some embodiments, the alert is indicated by one or more indicating lights 532. In some embodiments, the alert is stored in the central computer and presented in a compliance report. In some embodiments, after a threshold number of times the additional time input is activated over a set time period, no additional amount time is added, even though the additional time is requested.

In some embodiments, such as, for example, when a physical therapist is working with a patient, only one opportunity should be counted toward the physical therapists compliance metric when the physical therapist enters the room and one opportunity should be counted upon the final exit of the room by the physical therapist. Often a physical therapist needs to get a patient up and walking. Often the physical therapist is required to keep "hands on" the patient and walk the patient out into the hallway and around the floor. An opportunity should not be logged and counted each time the person enters or exits the room with the patient or when the physical therapist and the patient are walking around the room. In such cases, the additional time input for the role of a physical therapist may be a "freeze" input that can be unfrozen by the therapist. In some embodiments, the additional time input is a function of the persons role. For example, if the additional time input is for a nurse, the additional time may be, for example, 3 minutes. If, as in the present example, the person's role is a physical therapist, the additional time may be, for example, 20 minutes, or 30 minutes, or the like that corresponds to the amount of time the physical therapist is assigned to work with the patients.

Figure 6A:
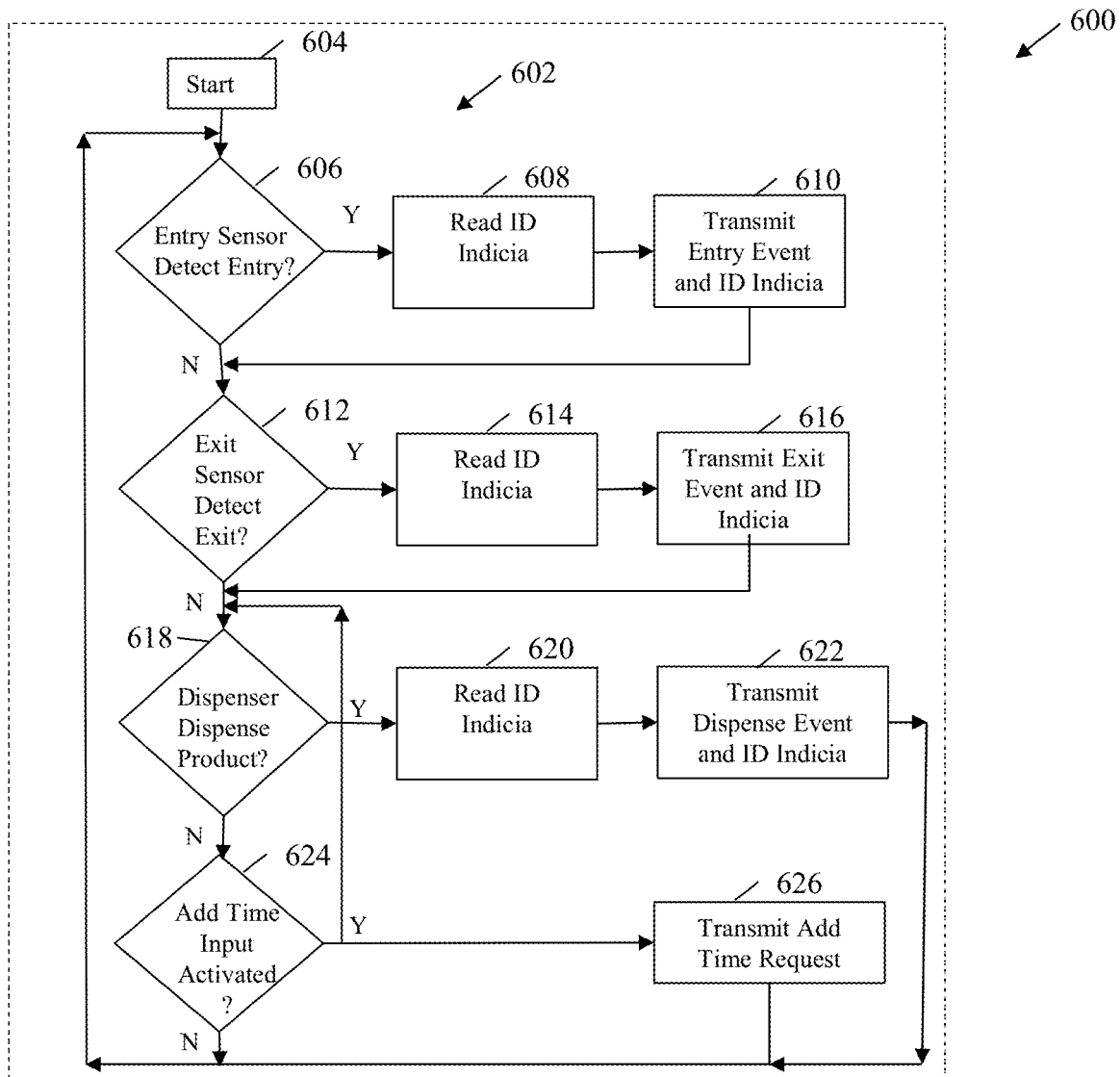
FIGS. 6A and 6B are an exemplary methodology for utilizing the additional time inputs in obtaining more accurate hand hygiene compliance metrics.
Figure 6B:
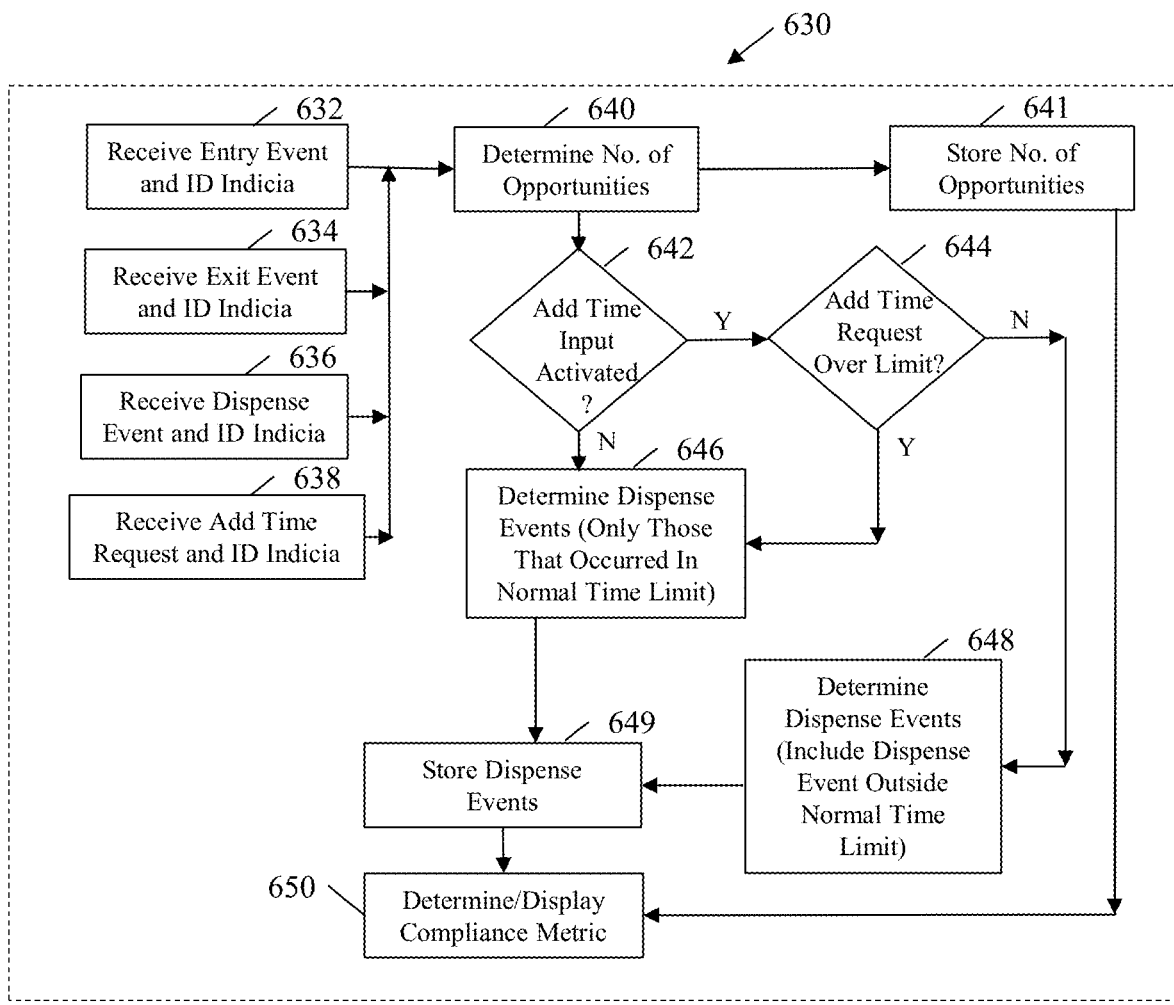

FIGS. 6A and 6B illustrate an exemplary methodology for an improved hand hygiene compliance system 600 having a time add feature. As discussed above, the exemplary methodologies described herein may have more of fewer blocks than shown and disclosed herein. In addition, unless noted otherwise, the blocks may be performed in different orders. In addition, in some embodiments, blocks or steps from other exemplary methodologies may be incorporated in this methodology. The exemplary methodology begins at block 604. At block 606 a determination is made as to whether an entry sensor detected entry to a room or area. The entry may be detected by, for example, a people counter as described above. If no entry has been detected the methodology flows to block 612. If an entry has been detected, identification indicia of the person entering the room is read at block 608. The indicia may be obtained through any means, including those described above, such as, for example, reading a transmission from a badge, requesting a transmission from the badge. After the identification ("ID") indicia is obtained, the system transmits an entry event and ID indicia to a central computer at block 610. In some embodiments, a central computer is not us used and relevant or desired calculations and number of opportunities occurring are calculated locally. In some embodiments, the entry event and/or ID indicia are stored in the badge. In some embodiments, the entry event and/or ID indicia are stored in the people counter or entry sensor. The exemplary methodology flows to block 612.

At block 612 a determination is made as to whether an exit sensor detected a person exiting the room or area. The exit may be detected by, for example, a people counter as described above. If no exit has been detected the methodology flows to block 618. If an exit has been detected, ID indicia of the person exiting the room is read at block 614. The ID indicia may be obtained through any of the manners described above, such as, for example, reading a transmission from a badge or requesting a transmission from the badge. After the ID indicia is obtained, the system transmits an entry event and ID indicia to a central computer at block 616. In some embodiments, a central computer is not us used and relevant calculations and number of opportunities occurring are calculated locally. In some embodiments, the exit event and/or ID indicia are stored in the badge. In some embodiments, the exit event and/or ID indicia are stored in the people counter or exit sensor. The exemplary methodology flows to block 618.

At block 618 a determination is made as to whether a dispenser has dispensed product. The dispense event may be detected by, for example, a smart dispenser or a dispenser having a compliance module associated therewith, such as, for example, those described above. If no dispense event has been detected the methodology flows back to block 606. If a dispense event has been detected, ID indicia of the person that receive the dose of product is read at block 620. The ID indicia may be obtained through any means, such as, for example, reading a transmission from a badge. After the ID indicia is obtained, the system transmits the dispense event and ID indicia to a central computer at block 622. In some embodiments, a dispenser ID and/or dispenser location is also transmitted. In some embodiments, a central computer is not us used and relevant calculations and number of dispense events occurring are tabulated locally. In some embodiments, the dispense event and/or ID indicia are stored in the dispenser. In some embodiments, the exit event and/or ID indicia are stored in the people counter or entry/exit sensor.

If no dispense event has been detected, the exemplary methodology flows to block 624 where a determination is made as to whether the user or healthcare worker requested "additional time" to obtain a dose of soap or sanitizer, and to thereby trigger a dispense event. If no request has been made, by for example, pressing an "additional time" button on the badge, the methodology loops back to block 606. If a request has been made, the request is transmitted to the central computer at block 626 and the methodology loops back to block 618 to see if a dose of product is dispensed within the additional time.

Entry events and ID indicia are received at block 632. Exit events and ID indicia are received at block 634. Dispense events and ID indicia are received at block 636. Requests for additional time are received at block 638. The events may be transmitted with a time stamp indicative of when the event occurred. In some embodiments the time stamp is added to the signals prior to transmission. In some embodiments, the time stamp is added during the transition, by for example, an intermediate transmission device, e.g. a gateway. In some embodiments, the time stamp is added upon receipt of the transmission by the central computer.

At block 640 the number of opportunities are determined. In some embodiments, there is only one opportunity, e.g. only one entry event or only one exit event. In some embodiments, there are more than one opportunities, e.g.

there have been multiple entries/exits for the person and the compliance metric derived from multiple opportunities and multiple dispense events. The number of compliance opportunities are stored at block 641. In some embodiments, the term "cumulative" is only a single event.

In some embodiments, the compliance metric, which in its simplest form is the number of dispense events divided by the number of "opportunities", is updated each time a new opportunity and its corresponding dispense event occurs (or no dispense event occurs). The compliance metric or compliance rate may compiled over any set period of time. In some embodiments, the compliance metric starts off fresh each day or each shift. In some embodiments, the compliance metric is calculate each time an opportunity occurs and a dispense event occurs or the period of time for the dispense event to occur expires and resets each time a new opportunity arises. Thus, the person is either currently compliant or not currently compliant. In some embodiments, the compliance metric is a cumulative metric that is reset at a set period, such as, for example once a day, once a week, once a month, or any other suitable period. In a preferred embodiment, each time and opportunity or corresponding dispense event is logged (or no dispense event is logged in the allotted period of time), the methodology is used to determine or update the compliance metric.

At block 642, a determination is made as to whether a request for additional time was made to trigger a dispense event with respect to a logged opportunity. If no additional time was requested by the badge wearer the methodology flows to block 646 and only dispense events that occurred within the standard time limits are determined at block 646. The number of dispenser events may be zero, if no dispense events occurred within the requisite time limits or the number of dispense events may be one, or may be more than one dispense events that occurred within the requisite time limits.

In some embodiments, if multiple dispense events occur prior to or immediately after an opportunity occurred, only one dispense event is used for the compliance metric for that time period. Using only one dispense event per set time period may prevent people from "gaming" the system by unnecessarily increasing the number of dispense events when there is no need to obtain a dose of product, because no new opportunity existed. The number of cumulative dispense events are stored at block 649. In some embodiments, the "cumulative" dispense events may be one or less. After the number of dispense events are determined, the compliance metric is determined at block 650 as a function of the qualifying cumulative opportunities and qualifying cumulative dispense events. The compliance metric may be displayed on a display, it may be placed in a report, stored in the system, combinations thereof, and the like. In a preferred embodiment, the compliance metric is cumulative over a period of time and not merely calculated on an opportunity by opportunity basis.

If at block 642 it is determined that a request for additional time was made, a determination is made at block 644 of whether too many requests for additional time have been made by the badge wearer. If there have been too many request, the methodology flows to block 646 and only the dispense events that occurred in the requisite time period are used. If at block 644 it is determine that the number of requests for additional time is lower than a selected threshold number of requests, the number of dispense events are determined at block 648. The number of dispense events includes the number of dispense events that occurred within the additional time allowed. The methodology flows back to block 650 where the compliance metric is determined by comparing the cumulative opportunities to the cumulative dispense events.

Figure 7:
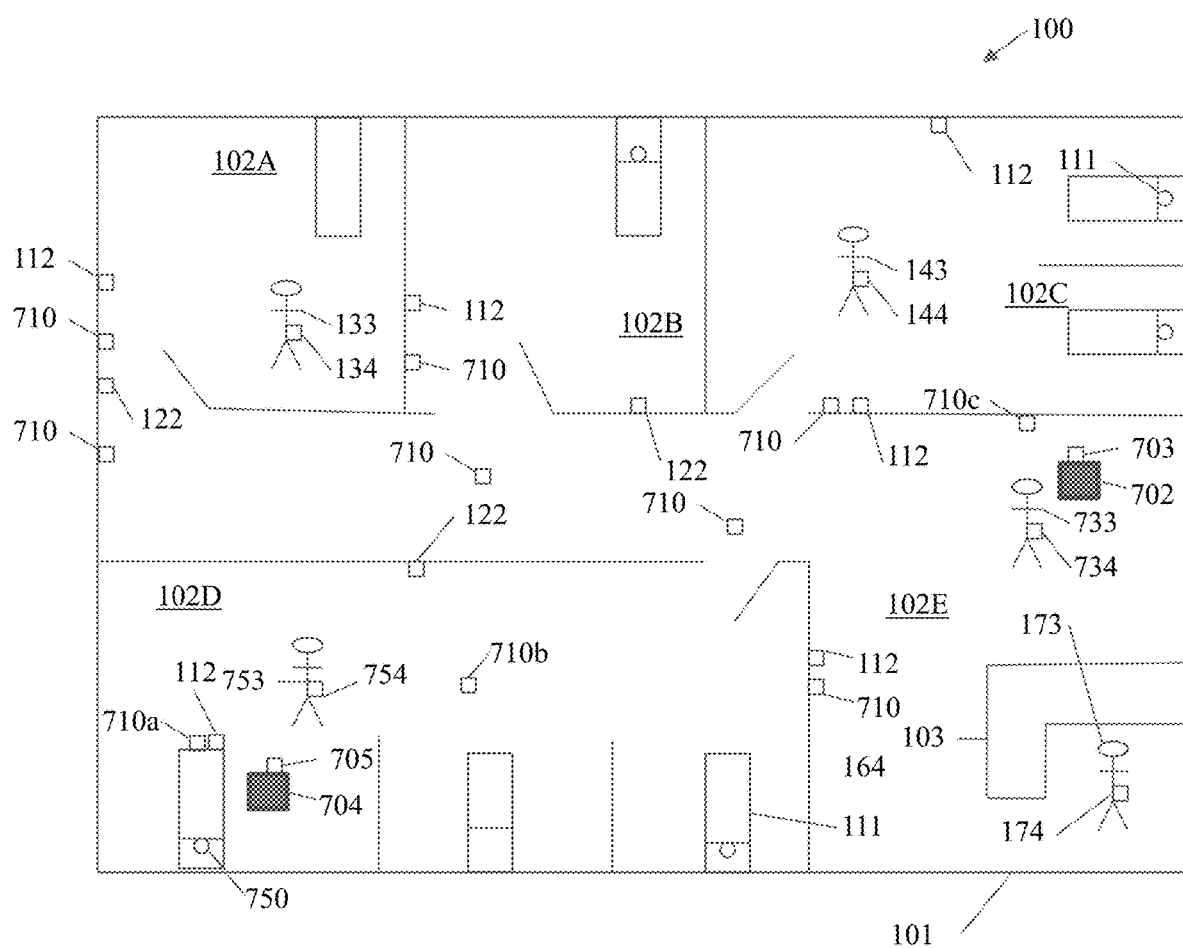
FIG. 7 is a simplified schematic diagram of an exemplary embodiment of an electronic automated monitoring system.

FIG. 7 is a simplified schematic diagram of an exemplary embodiment of an electronic automated monitoring system 700. FIG. 7 is similar to FIG. 1 and like reference numbers may not be not re-described herein. FIG. 7 illustrates a floor 101 of a hospital. There are a plurality of people counters 110 configured to detect the presence of an identification device, such as a badge or tag. In FIG. 7, assets 702 and 704 are included. Assets 702, 704 may be different types of medical equipment or hospital service equipment. For example, assets 702, 704 may be one or more of: wheel chairs, IV poles, EKG machines, respirators, crash carts, surgical carts, oxygen monitors, bear hugger machines, medical carts, food carts, janitorial carts, medical waste carts, and the like. Some assets may be disposable, such as, for example procedure kits, catheters, wound dressing, etc. Assets may be EVS assets, such as, cleaning supplies, linens, etc. Each of these types of assets has a role. The role of the asset may be used to determine whether an opportunity for a hand hygiene event has occurred. In some embodiments, the role of the asset and the roll of a health care worker may be used to determine whether an opportunity for a hand hygiene event has occurred.

Assets 702, 704 include badges or tags 703, 705 respectively. The badges or tags 703, 705 may be substantially the same as badges or tags 734, 754 worn or carried by persons 733, 753 respectively. There are a plurality of people sensors 710 (some of them are more specifically identified as 710a, 710b and 710c). People sensors 710 detect the presence of people or assets in the areas monitored by the people sensors 710. In this exemplary embodiment, people counter 710c may determine that asset 702 is located in the area monitored by people counter 710c. Badge 703 communicates with people sensor 710c and transmits data or information relating to asset 703. The data or information is indicative of the type of asset or role of the asset. In some embodiments, badge 703 transmits on or more of: a serial number, an asset type, usage information, sanitation status, last sanitation time and/or date, and the like. People counter 710c transmits information back to a remote computer (not shown). The information may include information or data indicative of the location of people counter 710a or a discrete identification code, time and asset 704 information. People counter 710c also detects the presence of person 733 and retrieves information relating to person 733 from badge or tag 734. The information may be any of the information disclosed herein, such as, for example, information indicative of the person and/or the role of the person. The information and the location are transmitted back to a remote computer. In this case, asset 702 may be a cleaned or sanitized asset that has not been in proximity of a patient.

In this exemplary embodiment, people sensor 710a detects asset 704 by detecting badge 705. Badge 705 communicates with people sensor 710a and transmits data or information relating to asset 704. The data or information is indicative of the type of asset or the role of the asset. In some embodiments, badge 705 transmits on or more of: a serial number, an asset type, usage information, sanitation status, last sanitation time and/or date, and the like. People counter 710a transmits information back to a remote computer (not shown). The information may include information or data indicative of the location of people counter 710a or a discrete identification code, time and asset 704 information, such as, for example, role of asset information. People counter 710a is monitoring the area around patient 750, and accordingly, because asset 704 was detected by people counter 710a, a determination may be made that asset 704 has been in proximity of patient 750. Thus, it may often be presumed that asset 704 needs to be cleaned or sanitized before it is used. In addition, if person 754 moves, uses, or in some cases is merely close to asset 704, it may often be presumed that person 754 may have triggered an opportunity event that requires person 754 wash or sanitize her hands. However, these presumptions may not always be a correct presumption. In some instances, based on the role of the asset 704, no opportunity for a hand hygiene event has occurred. Accordingly, it is important to know the role of the asset. For example, if the role of the asset is an IV stand, and the has not been used on a patient, but has been moved from one room to another, no hand hygiene opportunity has been created. Similarly, if the asset is a dirty clothes bin that does not have any dirty clothes located therein, contact with the asset may not result in a hand hygiene event. Other examples, include, for example, an EKG machine is typically handled by an EKG technician. Generally a person is laying in a prone position, the technician attaches disposable electrodes to the patient and hooks up the EKG machine. When the test is completed, the technician removes the leads and then removes the disposable electrodes from the patient. Another person that comes into contact with the EKG machine that is not performing EKGs would not cause an opportunity to be logged and counted in that person's compliance rate.

In addition, not every person who comes in contact with asset 704 after asset 704 has been in proximity of patient 750 triggers an opportunity for a hand hygiene event. Accordingly, to have an accurate compliance metric, one may desire to consider the role of person 754 in determining whether an opportunity should be logged and/or counted in person 754's hand hygiene compliance metric. For example, if person 754 has the role of a doctor, a nurse, physical therapist, or a technician, contact with asset 704 results in an opportunity that is logged and/or counted in person 754's compliance metric or compliance rate. If however, person 754 has the role of an aid, a janitorial staff, a counselor, an administrator or the like, no opportunity for a hand hygiene event is logged and/or counted for person 754.

Accordingly, more accurate compliance metrics or rates may be obtained for the health care worker based on one or more of the role of asset, proximity with a patient, role of the health care worker and her contact with assets.

As noted above, the exemplary mythologies or logic diagrams may contain additional blocks, may have fewer blocks, may combine two or more blocks into one step, may expand one or more blocks into additional steps and the like. For example, if the role of the health care worker is not being used, that information need not be collected.

Figure 8:
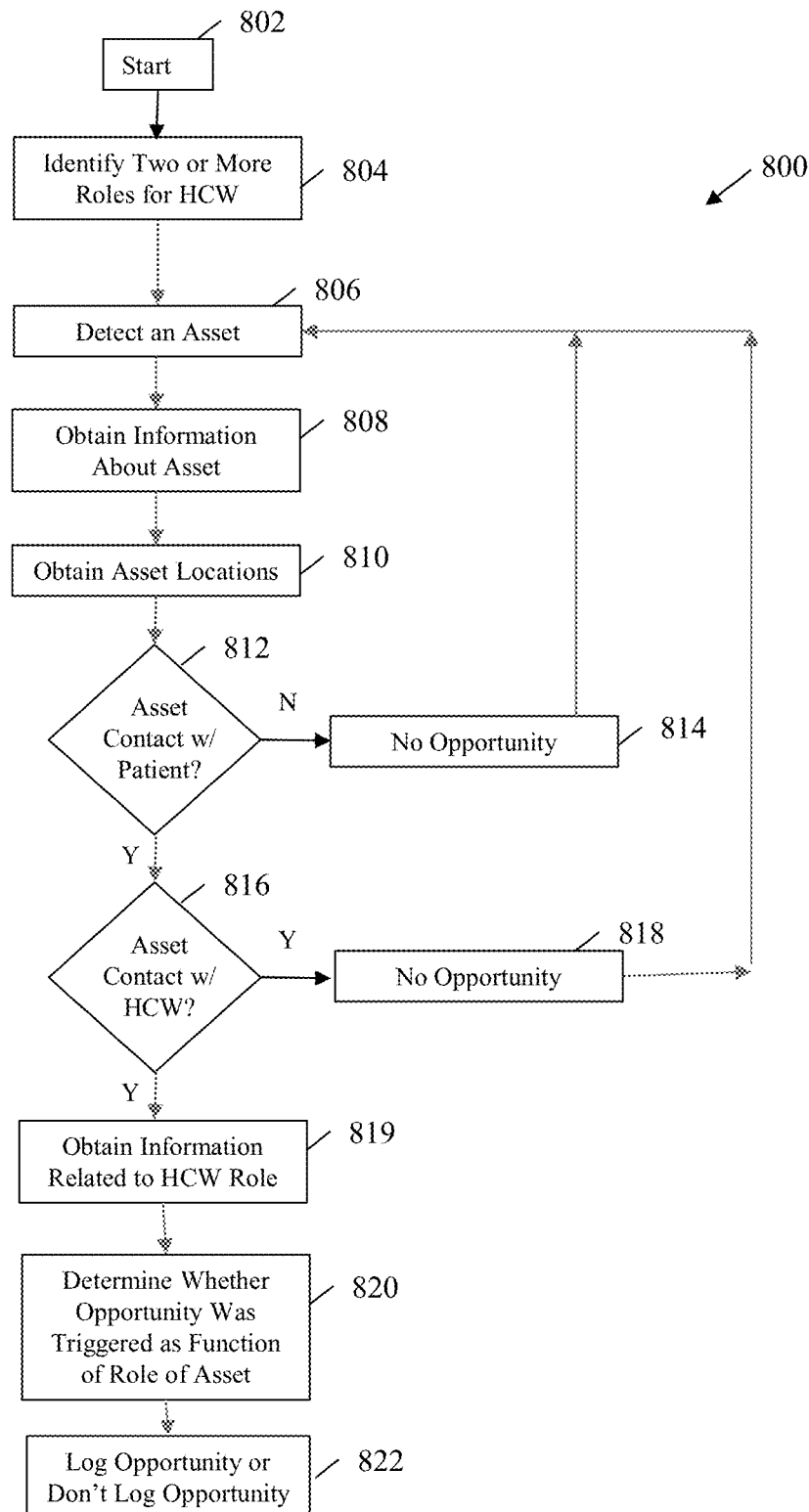
FIG. 8 is an exemplary methodology for determining a hand hygiene compliance opportunity as a function of an asset and a health care worker's role.

FIG. 8 illustrates an exemplary methodology 800 for determining whether or not an opportunity for a hand hygiene event has occurred and should be logged and/or counted. The exemplary methodology begins at block 802 and at block 804 two or more roles are identified for health care workers. The two or more roles may include two or more of: doctors, residents, nurses, therapists, janitors, aids, counselors, administrators, supervisors, maintenance workers, and the like. At block 806 an asset is detected or identified. At block 808 information relating to the asset is obtained. The information may be, for example, the role of the asset, one or more of a serial number, an asset type, usage information, sanitation status, last sanitation time and/or date, and the like. At block 810, the location information of the asset is determined. The location information may include the present location of the asset. In some embodiments, the location information includes data or information indicative of one or more prior locations of the asset. In some embodiments, the location information includes information indicative of all prior since the asset has been cleaned or sanitized.

At block 812, a determination is made as to whether the asset has been in proximity with a patient. The determination is made by review of the location information of the asset, which may be current location information or past or prior location information. In addition, in some embodiments, a review of when the asset has been cleaned or sanitized is also used in the determination. In some embodiments, each time an asset is cleaned or sanitized, the prior locations of that asset are removed from the location data or information that is used to determine whether the asset has been in contact with a patient. If at block 812, it is determined that the asset was not in contact with a patient, no opportunity is logged at block 814 and the methodology flows back to block 806. If it is determined that the asset has been in contact with a patient, a determination is made at block 816 as to whether a health care worker has been in contact with the asset. If no healthcare worker has been in contact with the asset, no opportunity is logged at block 818, and the methodology flows back to block 816.

If the asset has been in contact with a health care worker at block 816, information about the health care worker may be obtained at block 819. In some embodiments, the information about the health care worker also includes the role of the health care worker. Preferably, the information includes an identifier of that specific healthcare worker.

At block 820, a determination is made as to whether an opportunity for a hand hygiene event has occurred for the health care worker that is a function of the health care worker's contact with the asset and the role of the asset. At block 822, an opportunity for a hand hygiene event is either logged and counted has an opportunity for the heath care worker to perform a hand hygiene function, such as, washing or sanitizer her hands, in her compliance metric or compliance rate, or no opportunity is logged and/or counted for that health care worker and no opportunity for this event is counted in her compliance metrics or compliance rate.

Another method of determining hand hygiene opportunities includes identifying two or more roles for hospital workers, providing an asset and obtaining information related to the asset. The methodology further includes providing a sensor configured to determine a location of the asset, determining whether the asset has been in the proximity of a patient and determine that a hospital worker has come in contact with the asset. The methodology further includes determining whether the contact between the hospital worker and the asset triggered a hand hygiene opportunity as a function of the role of the asset. Determining whether the contact triggered a hand hygiene opportunity is a function of the information related to the role of the asset and the hospital worker.

Another exemplary methodology for determining hand hygiene opportunities includes providing an asset, obtaining information related to the type of asset, providing a sensor configured to determine a location of the asset, determining whether the asset has been in the proximity of a patient, determining that a hospital worker has come in contact with the asset and determining whether the contact between the hospital worker and the asset triggered a hand hygiene opportunity. Determining whether the contact triggered a hand hygiene opportunity is a function of the information related to the type of asset.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

We claim:

1. A method of determining hand hygiene compliance in a hospital comprising:
   identifying two or more roles;
   assigning a role to a person;
   providing a sensor configured to determine an entry event that is a function of the person's entry into a selected area and wirelessly transmit a signal indicative of the entry event;
   determining that a person has entered the selected area;
   obtaining an identifier of the person that is indicative of the person's role;
   providing a sensor configured to determine an exit event that is a function of the person's exit from the selected area and wirelessly transmit a signal indicative of an exit event;
   determining that a person has exited a selected area;
   determining whether the entry event into the area triggered a hand hygiene opportunity; and
   determining whether the exit event from the area triggered a hand hygiene opportunity;
   wherein determining whether the entry event and/or the exit event triggered a hand hygiene opportunity is a function of the role of the person.

2. The method of claim 1 wherein an entry event does not trigger a hand hygiene event for one or more roles.

3. The method of claim 1 wherein the two or more roles include at least one role selected from the group of a physician, a resident, a nurse, a technician, a phlebotomist, an aid, a cleaning staff, a maintenance staff, a food currier, and a visitor.

4. The method of claim 1 comprising determining that two or more people assigned to the same role entered the selected area and wherein the number of hand hygiene opportunities determined is less than the number of the two or more people.

5. The method of claim 1 wherein one or more roles allow multiple entry events and/or exit events within a time period without triggering a hand hygiene opportunity.

6. The method of claim 1 further comprising providing a sensor to determine whether a person is bringing an object into the selected area and if the person is bringing an object into the selected area, the determining step determines that no hand hygiene opportunity is triggered as a function of the entry event.

7. The method of claim 6 wherein the object is a piece of medical equipment.

8. The method of claim 6 wherein the object is food service equipment.

9. The method of claim 1 wherein determining whether an entry event has occurred is further a function of time that the health care worker remained in the area.

10. The method of claim 1 if the persons role is one of a cleaning staff and a maintenance staff the determining whether a hand hygiene opportunity is triggered is a function of the last exit event by the person.

11. The method of claim 1 wherein an entry event does not trigger a hand hygiene opportunity if the person's role is one of a cleaning staff, a maintenance worker and a visitor.

12. The method of claim 1 further comprising determining that a role is one or more doctor or residents that entered the selected area and determining whether a hand hygiene opportunity is triggered is a function of a doctor and one or more residents entering the selected area and the number of hand hygiene opportunities that are triggered is less than the total amount of doctors and residents that have entered the selected area.

13. A method of determining hand hygiene opportunities comprising:
   obtaining information related to a selected area of a hospital;
   providing a sensor configured to determine an entry event that is a function of a person's entry into the selected area;
   wherein the sensor comprises wireless communication circuitry for transmitting a signal indicative of the entry event;
   obtaining a signal that a person has entered the selected area;
   determining whether the entry event into the area triggered a hand hygiene opportunity;
   providing a dispenser for dispensing a product;
   determining if a dispense event has occurred;
   determining whether to credit the person with a dispense event;
   wherein determining whether the entry event triggered a hand hygiene opportunity is a function of the information related to the selected area.

14. The method of claim 13 wherein the information related to a selected area comprises whether the selected area is occupied by a patient.

15. The method of claim 13 wherein the information related to a selected area comprises information indicative of contact precautions.

16. The method of claim 15 wherein the contact precautions are indicative of a C-Difficile infection.

17. The method of claim 16 wherein determining whether to credit the person with a dispense event is a function of whether the dispense event is a soap dispense.

18. A method of determining hand hygiene opportunities comprising:
- identifying two or more roles for hospital workers;
- providing an asset;
- obtaining information related to the asset;
- providing a sensor configured to determine a location of the asset;
- determining whether the asset has been in the proximity of a patient;
- determine that a hospital worker has come in contact with the asset;
- determining whether the contact between the hospital worker and the asset triggered a hand hygiene opportunity;
- wherein determining whether the contact triggered a hand hygiene opportunity is a function of the information related to the asset and the role of the hospital worker.

19. The method of claim 18 wherein a hand hygiene opportunity occurs if the role of the hospital worker is to handle the type of asset.

20. The method of claim 18 wherein the asset is a medical device.

* * * * *